(12) United States Patent
Lugnani et al.

(10) Patent No.: US 11,857,240 B2
(45) Date of Patent: Jan. 2, 2024

(54) METHODS, SYSTEMS, AND APPARATUSES FOR CRYOSURGERY, COLDSURGERY, AND ELECTROLYSIS

(71) Applicant: CRYOELECTRIC SCIENCE LTD., Hong Kong (HK)

(72) Inventors: Franco Lugnani, Divaca (SI); Boris Rubinsky, El Cerrito, CA (US); Guojiang Zhao, Hong Kong (HK)

(73) Assignee: CRYOELECTRIC SCIENCE LTD., Hong Kong (HK)

( * ) Notice: Subject to any disclaimer, the term of this patent is extended or adjusted under 35 U.S.C. 154(b) by 857 days.

(21) Appl. No.: 16/742,624

(22) Filed: Jan. 14, 2020

(65) Prior Publication Data

US 2020/0222102 A1    Jul. 16, 2020

Related U.S. Application Data

(60) Provisional application No. 62/792,145, filed on Jan. 14, 2019.

(51) Int. Cl.
| | | |
|---|---|---|
| *A61B 18/02* | (2006.01) | |
| *A61B 17/00* | (2006.01) | |
| *A61B 18/00* | (2006.01) | |

(52) U.S. Cl.
CPC .... *A61B 18/02* (2013.01); *A61B 2017/00097* (2013.01); *A61B 2018/00101* (2013.01); *A61B 2018/0262* (2013.01)

(58) Field of Classification Search
CPC ............... A61B 18/02; A61B 18/1477; A61B 2018/00101; A61B 2018/00892;
(Continued)

(56) References Cited

U.S. PATENT DOCUMENTS

| | | |
|---|---|---|
| 5,254,116 A | 10/1993 | Baust et al. |
| 5,334,181 A | 8/1994 | Rubinsky et al. |

(Continued)

FOREIGN PATENT DOCUMENTS

| | | |
|---|---|---|
| WO | 2017123981 A1 | 7/2017 |
| WO | 2017143269 A1 | 8/2017 |

OTHER PUBLICATIONS

International Search Report and Written Opinion of International Application No. PCT/US20/13532 dated Apr. 9, 2020.
(Continued)

*Primary Examiner* — Khadijeh A Vahdat
(74) *Attorney, Agent, or Firm* — DINSMORE & SHOHL LLP

(57) ABSTRACT

A cryosurgical instrument having a cryosurgical probe, at least one electrode configured to generate products of electrolysis, and a protective member coupled to at least a portion of an exterior surface of the cryosurgical probe effective to substantially isolate the cryosurgical probe from the products of electrolysis is disclosed. Methods of providing combined cryosurgical treatment and electrolysis with the cryosurgical instrument are disclosed. A system having the cryosurgical instrument, a cryogenic power supply, an electrolysis power supply, and a controller configured to generate a cryogenic signal and an electric signal is disclosed. Methods of producing the cryosurgical instrument by selecting a cryosurgical probe, coupling at least one electrode to the cryosurgical probe, and fastening the protective member to at least a portion of an exterior surface of the cryosurgical probe are disclosed. Cryosurgical probe protective devices are also disclosed.

23 Claims, 12 Drawing Sheets

(58) Field of Classification Search
CPC .... A61B 2018/0262; A61B 2018/1266; A61B 2017/00097
See application file for complete search history.

(56) References Cited

U.S. PATENT DOCUMENTS

| | | | |
|---|---|---|---|
| 5,513,742 | A | 5/1996 | Hulse et al. |
| 5,654,279 | A | 8/1997 | Rubinsky et al. |
| 5,800,487 | A | 9/1998 | Mikus et al. |
| 5,800,488 | A | 9/1998 | Crockett |
| 5,910,104 | A | 6/1999 | Dobak, III et al. |
| 5,978,697 | A | 11/1999 | Maytal et al. |
| 6,021,347 | A | 2/2000 | Herbst et al. |
| 6,139,544 | A | 10/2000 | Mikus et al. |
| 6,142,991 | A | 11/2000 | Schatzberger |
| 6,179,831 | B1 | 1/2001 | Bliweis |
| 6,366,808 | B1 | 4/2002 | Schroeppel et al. |
| 6,379,348 | B1 | 4/2002 | Onik |
| 6,471,694 | B1 | 10/2002 | Kudaravalli et al. |
| 6,475,212 | B2 | 11/2002 | Dobak, III et al. |
| 6,699,282 | B1 | 3/2004 | Sceusa |
| 6,738,663 | B2 | 5/2004 | Schroeppel et al. |
| 6,901,296 | B1 | 5/2005 | Whitehurst et al. |
| 6,902,564 | B2 | 6/2005 | Morgan et al. |
| 6,929,668 | B2 | 8/2005 | Millet et al. |
| 6,963,770 | B2 | 11/2005 | Scarantino et al. |
| 6,963,771 | B2 | 11/2005 | Scarantino et al. |
| 7,079,890 | B2 | 7/2006 | Ahn et al. |
| 7,412,285 | B2 | 8/2008 | Schroeppel et al. |
| 7,445,619 | B2 | 11/2008 | Auge, II et al. |
| 7,526,334 | B2 | 4/2009 | Herbst et al. |
| 7,713,269 | B2 | 5/2010 | Auge, II et al. |
| 7,720,549 | B2 | 5/2010 | Schroeppel et al. |
| 7,742,811 | B2 | 6/2010 | Schroeppel et al. |
| 7,756,568 | B2 | 7/2010 | Scarantino et al. |
| 7,769,431 | B2 | 8/2010 | Scarantino et al. |
| 7,771,422 | B2 | 8/2010 | Auge, II et al. |
| 7,819,864 | B2 | 10/2010 | Morgan et al. |
| 8,014,854 | B2 | 9/2011 | Schroeppel et al. |
| 8,024,048 | B2 | 9/2011 | Schroeppel et al. |
| 8,048,067 | B2 | 11/2011 | Davalos et al. |
| 8,321,009 | B2 | 11/2012 | Rosemberg |
| 8,343,147 | B2 | 1/2013 | Rosemberg |
| 8,591,508 | B2 | 11/2013 | Morgan et al. |
| 8,600,494 | B2 | 12/2013 | Schroeppel et al. |
| 9,211,155 | B2 | 12/2015 | Fruland et al. |
| 9,597,145 | B2 | 3/2017 | Nelson et al. |
| 10,085,800 | B2 | 10/2018 | Nelson et al. |
| 2002/0111612 | A1 | 8/2002 | Lalonde et al. |
| 2003/0171742 | A1* | 9/2003 | Mihalik ............ A61M 25/0029 606/22 |
| 2004/0000158 | A1* | 1/2004 | Luo ...................... F25B 19/005 62/259.3 |
| 2013/0012938 | A1 | 1/2013 | Asirvatham et al. |
| 2014/0088578 | A1 | 3/2014 | Rubinsky et al. |
| 2016/0287867 | A1 | 10/2016 | Rubinsky et al. |
| 2016/0296269 | A1 | 10/2016 | Rubinsky et al. |
| 2019/0023804 | A1* | 1/2019 | Onik ................. C07K 16/2896 |

OTHER PUBLICATIONS

Arav A. et al. Phase transition temperature and chilling sensitivity of bovine oocytes. Cryobiology, vol. 33, issue 6, pp. 589-599, 1996.
C. Gilbert, G.H. Onik, W.K. Haddick, and B. Rubinsky, "The Use of Ultrasound Imaging for Monitoring Cryosurgery," IEEE Trans. of Biomed. Eng., BME-31, No. 8, 563, 1984.
Daniels CS, Rubinsky B (2011) Temperature Modulation of Electric Fields in Biological Matter. PLoS One 6(6): e20877. https://doi.org/10.1371/journal.pone.0020877.
Daniels, CS, Rubinsky B., 2011 Cryosurgery with Pulsed Electric Fields. PLoS One 6(11): e26219. doi:10.1371/journal.pone.0026219.
E. Nilsson, H. Von Euler, J. Berendson, A. Thorne, P. Wersäll, I. Näslund, A.S. Lagerstedt, K. Narfström, J.M. Olsson, Electrochemical treatment of tumours, Bioelectrochemistry Bioenerg. 51 (2000) 1-11. doi:10.1016/S0302-4598(99)00073-2.
Franco Lugnani, Fabrizio Zanconati, Thomas Marcuzzo, Cristina Bottin, Paul Mikus, Enric Guenther, Nina Klein, Liel Rubinsky, Michael K. Stehling, Boris Rubinsky A Vivens Ex Vivo Study on the Synergistic Effect of Electrolysis and Freezing on the Cell Nucleus, PLoS One, 10 (12) 2015, DOI: 10.1371/journal.pone.0145133.
H. von Euler, E. Nilsson, A.S. Lagerstedt, J.M. Olsson, Development of a dose-planning method for electrochemical treatment of tumors: A study of mammary tissue in healthy female CD rats, Electro- and Magnetobiology. 18 (1999) 93–+. doi:10.3109/15368379909012903.
Handbook of Electroporation, Damijan Miklavcic Ed. Springer Nature Switzerland AG 2018, <https://doi.org/10.1007/978-3-319-26779-1>.
Knight, John, R.P. Control of translation in the cold: implications for therapeutic hypothermia. Biochemical Science Transactions. vol. 33(3) p. 333-337, 2015.
Koushafar, H., Rubinsky. B., Effect of Antifreeze Proteins on frozen primary prostatic adenocarcinoma cells, Urology, vol. 49, n.3, pp. 421-425, 1997.
Lugnani, Franco; Gunther, Enric; Torrecillas, Pedro; Galacho, Carlos Jimenez; Garrido, Adolfo; Mikus, Paul; Klein, Nina; Stehling, Michael K; Macchioro, Matteo; Rubinsky, Liel; Raju, Narayan; Rubinsky, Boris. Cryoelectrolysis; an acute case study in the pig liver. Cryobiology vol. 78; pp. 110-114; DOI: 10.1016/j.cryobiol.2017.08.001; Published: Oct. 2017.
Lugnani, Franco; Macchioro, Matteo; Rubinsky, Boris. "Cryoelectrolysis—electrolytic processes in a frozen physiological saline medium," PEERJ vol. 5, Article No. e2810, Published: Jan. 17, 2017.
M. Phillips, N. Raju, L. Rubinsky, B. Rubinsky, Modulating electrolytic tissue ablation with reversible electroporation pulses, Technology. 3 (2015) 45-53. doi:10.1142/s233954781550003x.
Manstein, Dieter; Laubach, Hans; Watanabe, Kanna; et al., "Selective Cryolysis: A Novel Method of Non-Invasive Fat Removal," Lasers Surg. Med. 40:595-604, 2008. (c) 2008 Wiley-Liss, Inc.
Mir L M., Rubinsky B. Treatment of cancer with cryochemotherapy. British Journal of Cancer. 86(10). May 20, 2002. 1658-1660.
Mir, Luis et al. Electrochemotherapy potentiation of antitumour effect of bleomycin by local electric pulses. European journal of cancer & clinical oncology, 1991 vol. 27 iss:1 p. 68-72.
Mohammad Hjouj, Hanush Krishnan and Boris Rubinsky, Cryoelectrolysis for treatment of atrial fibrillation: a first order feasibility study. CryoLetters 38 (6), 428-433 (2017).
P. Mazur, Cryobiology: The Freezing of Biological Systems, Science (80–.). 168 (1970) 939-949. doi:10.1126/science.168.3934.939.
Phillips, M., L. Rubinsky, A. Meir, N. Raju, and B. Rubinsky. Combining electrolysis and electroporation for tissue ablation. Technol. Cancer Res. Treat. 14(4):395-410, 2015.
R. Davalos, L. Mir, B. Rubinsky, Tissue ablation with irreversible electroporation, Ann. Biomed. Eng. 33 (2) (2005) 223-231.
R. Goel, K. Anderson, J. Slaton, F. Schmidlin, G. Vercellotti, J. Belcher, J.C. Bischof, Adjuvant Approaches to Enhance Cryosurgery, J. Biomech. Eng. (2009). doi:10.1115/1.3156804.
Robert Amory, "A treatise on electrolysis and its application to therapeutical and surgical treatment in disease", New York, William Woof & Company, 56&58 Lafayette Place, 1886.
Rubinsky B. Ch 26—"Numerical Bio-Heat Transfer" in Handbook of Numerical Heat Transfer. Minkowycz, W.J., Sparrow, E.M., Murthy, J.Y. eds. John Wiley @Sons. Inc., 2006.
Rubinsky, Liel, Enric Guenther, Paul Mikus, Michael Stehling, and Boris Rubinsky. "Electrolytic Effects During Tissue Ablation by Electroporation." Technology in cancer research & treatment (2015): DOI 1533034615601549.
Rubinsky. B. "Cryosurgery" in Ann. Rev. Biomed. Engr. Eds. M.L. Yarmush, K.R. Diller, M. Toner, vol. 2, pp. 157-189, Annual Reviews, Palo Alto, 2000.
Rui, J., Tatsutani, K.N., Dahiya, R., Rubinsky, B. Effect of thermal variables on human breast cancer in cryosurgery. Breast Cancer Research and Treatment, 53 182-192, 1999.

(56) References Cited

OTHER PUBLICATIONS

Saulis, G., R. Lape, R. Praneviciute, and D. Mickevicius. Changes of the solution pH due to exposure by high-voltage electric pulses. Bioelectrochemistry. 67(1):101-108, 2005.

Stehling MK, Guenther E, Mikus P, Klein N, Rubinsky L, Rubinsky B (2016) Synergistic Combination of Electrolysis and Electroporation for Tissue Ablation. PLoS One 11(2): e0148317. doi:10.1371/journal.pone.0148317.

Tatsutani, K., Rubinsky, B., Onik, G., Dahiya, R., "Effect of thermal variables on frozen human prostatic adenocarcinoma cells." Urology. vol. 48 (3) pp. 441-447, 1996.

Thomas J. Manuel; Pujita Munnangi; Boris Rubinsky An Electrochemistry Study of Cryoelectrolysis in Frozen Physiological Saline IEEE Transactions on Biomedical Engineering Year: 2017, vol. vol. 64 Issue: 7 pp. 1654-1659 Published: Jul. 2017.

Turjanski, P., N. Olaiz, F. Maglietti, S. Michinski, C. Suarez, F. V. Molina, et al. The role of pH fronts in reversible electroporation. PloS One. 6(4):e17303, 2011.

Xiao, C. Rubinsky, B Theoretical analysis of AC electric field transmission into biological tissue through frozen saline for electroporation. Bioelectromagnetics vol. 35 Issue: 8 pp. 607-613 Published: Dec. 2014.

Supplemental European Search Report for European Application No. 20 741 253.7 (EP 20 74 1253) dated Oct. 13, 2021, 9 pages.

\* cited by examiner

METHODS, SYSTEMS, AND APPARATUSES FOR CRYOSURGERY, COLDSURGERY, AND ELECTROLYSIS

CROSS-REFERENCE TO RELATED APPLICATIONS

This application claims priority under 35 U.S.C. § 119(e) to U.S. Provisional Patent Application Ser. No. 62/792,145, titled "CSE Device Patent with Figures," filed Jan. 14, 2019, which is incorporated by reference herein in its entirety for all purposes.

FIELD OF TECHNOLOGY

Aspects and embodiments disclosed herein are generally related to cryosurgery probes, and more specifically, to cryosurgery probes used in combination cryosurgery and electrolysis treatments.

SUMMARY

In accordance with one aspect, there is provided a cryosurgical instrument. The cryosurgical instrument may comprise a cryosurgical probe configured to deliver a cryosurgical treatment to a target tissue. The cryosurgical instrument may comprise at least one electrode configured to generate products of electrolysis at the target tissue. The cryosurgical instrument may comprise a protective member coupled to at least a portion of an exterior surface of the cryosurgical probe. The protective member may be effective to substantially isolate the cryosurgical probe from the products of electrolysis.

In some embodiments, the protective member may be thermally conductive.

In some embodiments, the electrode may be fastened to the cryosurgical probe.

The electrode may be fastened to a portion of the exterior surface of the cryosurgical probe adjacent to the protective member.

In some embodiments, the electrode may be thermally conductive.

In some embodiments, at least one of the electrode and the protective member may be movable along the exterior surface of the cryosurgical probe.

In some embodiments, the electrode may be electrically wired as an anode and the cryosurgical probe may be electrically wired as the cathode.

The cryosurgical instrument may further comprise a vacuum layer between the exterior surface of the cryosurgical probe and the protective member.

The vacuum layer may be movable along the exterior surface of the cryosurgical probe.

In some embodiments, the protective member may be reversibly removable from the cryosurgical instrument.

In accordance with another aspect, there is provided a method of providing combined cryosurgical treatment and electrolysis. The method may comprise bringing the cryosurgical instrument into contact with the target tissue. The method may comprise delivering a cryosurgical treatment to the target tissue. The method may comprise generating products of electrolysis at the target tissue.

The cryosurgical treatment may comprise cooling to a temperature of between about 0° C. and about −40° C.

The products of electrolysis may be generated by an electrical current of between about 10 mA/cm$^2$ electrode surface to 200 mA/cm$^2$ electrode surface at a voltage of between about 5 V to 50 V.

The method may comprise independently controlling dosage, timing, and magnitude of the cryosurgical treatment and the electrolysis.

In accordance with another aspect, there is provided a cryosurgical system. The system may comprise a cryosurgical instrument comprising a cryosurgical probe configured to deliver a cryosurgical treatment to a target tissue, at least one electrode configured to generate products of electrolysis at the target tissue, and a protective member coupled to at least a portion of an exterior surface of the cryosurgical probe, effective to substantially isolate the cryosurgical probe from the products of electrolysis. The system may comprise a cryogenic power supply electrically connected to the cryosurgical probe. The system may comprise an electrolysis power supply electrically connected to the at least one electrode. The system may comprise a controller operatively connected to the cryogenic power supply and the electrolysis power supply. The controller may be configured to generate a cryogenic signal and an electric signal.

In some embodiments, the controller may be configured to control at least one parameter selected from dosage, timing, and magnitude of the cryosurgical treatment and the electrolysis.

The system may further comprise a pH sensor positioned to measure pH at the target tissue.

The pH sensor may be operatively connected to the controller. The controller may be configured to generate the electric signal responsive to the pH measurement.

The system may further comprise an electric meter positioned to measure electric field strength at the target tissue.

The electric meter may be operatively connected to the controller. The controller may be configured to generate the electric signal responsive to the electric field strength.

In accordance with another aspect, there is provided a method of producing a cryosurgical instrument. The method may comprise selecting a cryosurgical probe configured to deliver a cryosurgical treatment to a target tissue. The method may comprise coupling at least one electrode configured to generate products of electrolysis to the cryosurgical probe. The method may comprise fastening a protective member to at least a portion of an exterior surface of the cryosurgical probe, effective to substantially isolate the cryosurgical probe from the products of electrolysis.

The method may comprise selecting a material for the protective member to be thermally conductive and more anodic than a material of the cryosurgical probe.

The method may comprise positioning a vacuum layer between the external surface of the cryosurgical probe and the protective member.

In accordance with yet another aspect, there is provided a cryosurgical probe protective device formed of a material effective to substantially isolate the cryosurgical probe from products of electrolysis and being dimensioned to conform to at least a portion of an exterior surface of the cryosurgical probe.

The cryosurgical probe protective device may be configured to have a thickness effective to substantially isolate the cryosurgical probe from products of electrolysis when conformed to the at least a portion of the exterior surface of the cryosurgical probe.

In some embodiments, the material of the cryosurgical probe protective device may be more anodic than a material of the cryosurgical probe.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
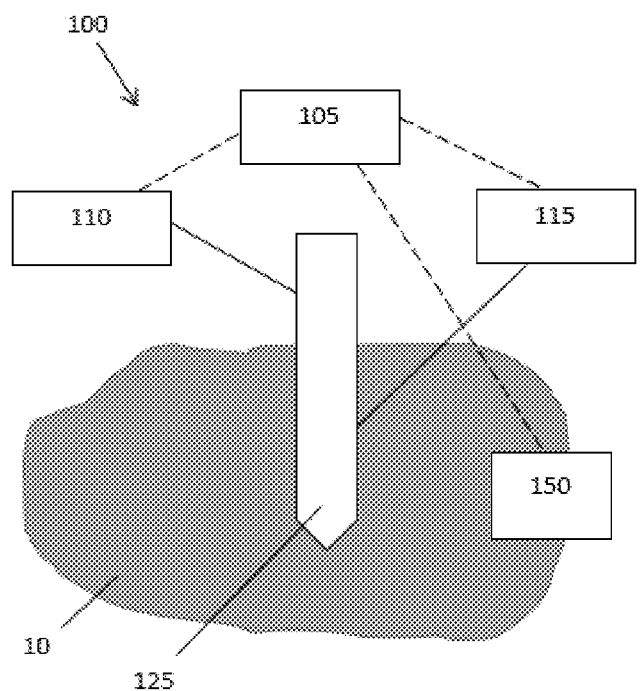
FIG. 1 is a schematic diagram of a cryosurgical system, according to one embodiment.

The disclosure relates generally to protection of cryosurgical probes from damage during a tissue ablation protocol that includes the generation of products of electrolysis. In particular, the tissue ablation protocol may involve a targeted cooling thermal surgical procedure and the products of electrolysis. The products of electrolysis may be generated before, during, and/or after the process of cryosurgery and/or cooling.

Minimally invasive tissue ablation procedures are commonly used in medicine. Ablation may generally refer to the cessation of biological viability. Ablation surgeries may employ various biophysical phenomena that ablate cells and tissues and various devices and technologies that can generate the ablation biophysical phenomena. Cell ablation may be performed through thermal ablation treatment. For example, temperatures above physiological temperature may be used for cell ablation. Heat treatment may be accomplished through the delivery of radiofrequency energy, microwave energy, Joule heating energy, laser energy, ultrasound energy, and combinations thereof to the target tissue sites. Temperatures below physiological temperature may be used for cell ablation. Cooling treatment may be accomplished cooling probes at the target tissue sites. Cryosurgery is one example of a thermal cooling cell ablation technology. Cryosurgery involves the use of a device, for example, a cryosurgical probe, that removes energy and thereby generate temperatures near or below the freezing temperature of the tissue at the target tissue site.

Non-invasive medical imaging can be employed with thermal ablation treatments to monitor the extent of heating or freezing in real time. Real time imaging may provide additional control over the thermal treatment.

Non-thermal ablation technologies include electrolysis and electroporation. Tissue ablation by electrolysis generally involves the passage of electrical currents between a pair of electrodes and the tissue. The process of electrolysis occurs at the electrode surface in contact with an ionic solution. During electrolysis, typically, new chemical species are generated at the interface between the electrodes and the ionic solution as a result of the electrical potential driven transfer between the electrons and ions and atoms at the electrode. The products of electrolysis may diffuse from the electrodes by thermal diffusion and electro osmosis. Tissue ablation may be caused by development of a cytotoxic environment due to local changes in pH and/or the generation of products of electrolysis at the electrode surface.

Electroporation typically involves electric pulses which permeabilize the cell membrane and thereby cause cell death. Tissue ablation may be caused by non-reversible permeabilization of the cell membrane and/or the entry of toxic compounds into the membrane permeabilized cell. Electroporation, which involves the passing of an electric current from electrodes to tissue, may also generate products of electrolysis. Tissue ablation procedures that combine electroporation with electrolysis (purposefully or inadvertently) may also be employed. The combined effect of electroporation and electrolysis may enhance the ablation.

Certain ablation procedures combine electrolysis (either from an electrolysis procedure or generated by an electroporation procedure) with cold thermal ablation, for example, cryosurgery. Such procedures may be employed to augment cell death in the subfreezing region of tissue, where cells may be frozen but survive the cryosurgery. However, the products of electrolysis may cause damage to cryosurgical probes, potentially jeopardizing the safety of the user and the patient. Methods and devices that inhibit or reduce damage to cryosurgical probes when contacted with products of electrolysis are disclosed herein.

Thus, the methods, systems, and devices disclosed herein may protect cryosurgery probes from damage during a tissue ablation procedure which includes a combination of cold thermal ablation and an electric process that generates products of electrolysis.

In accordance with one aspect, there is provided a cryosurgical instrument for performing cryoelectrolysis. The cryosurgical instrument may comprise a cryosurgical probe configured to deliver a cryosurgical treatment to a target tissue. The cryosurgical probe is a device capable of bringing the target tissue to a desired cold temperature. In general, the cryosurgical probe may operate by bringing its external surface to a target temperature. The external surface may be brought into contact with the target tissue to be cooled, for example, ablated. The freezing may propagate from the part of the cryosurgical probe at subfreezing temperatures outward into the tissue.

Figure 2:
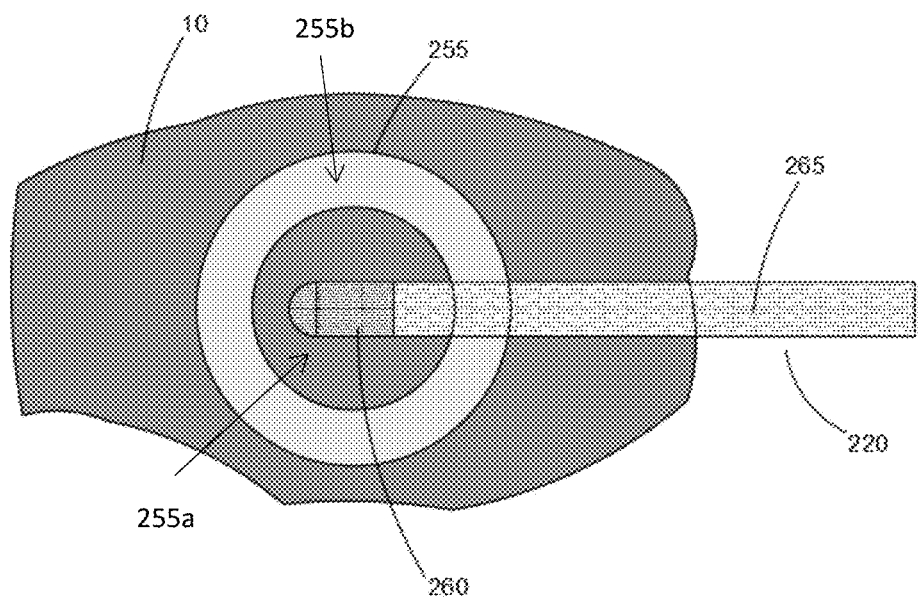
FIG. 2 is a schematic diagram of a cryosurgical probe in use, according to one embodiment.

FIG. 2 is a schematic drawing of an exemplary cryosurgical probe 220 in tissue 10 and the tissue ice ball 255 (cooled region at sub-physiological temperatures) that forms around the cryosurgical probe 220. The cryosurgical probe may be thermally conductive. In some embodiments, the cryosurgical probe may comprise one portion that is thermally conductive 260 (i.e., not thermally insulated) which extracts the energy from the tissue 10, and one portion that is thermally insulated 265. Formation of the ice ball 255 in tissue is confined to the vicinity of the thermally conductive portion 260.

The cryosurgical probe may be configured to perform cryosurgical ablation. The cryosurgical probe may include one or more probes through which a cryogen is internally circulated to cool the probe. Thermal conduction of the cryogen through the probe wall may operate to cool the target tissue when the probe is placed in contact with the target tissue.

Cryosurgical probes may bring their external surface to a target temperature by a variety of methods. Typically, the cooling of the cryosurgical probe may be done by circulating a pressurized fluid (gas or liquid) through the cryosurgical probe. Certain cryosurgical probes may be cooled by boiling off a cryogen. Other cryosurgical probes may be cooled by Joule Thomson expansion of high-pressure gases. In general, the interior volume of the cryosurgery probe may be at an elevated pressure, for example, during cooling.

The cryosurgical probe may generally include a shaft with a sharp or blunt tip. The cryosurgical probe may be dimensioned for parenteral use. For example, the cryosurgery probe may be thin. The cryosurgery probe may be structured for parenteral use. For example, the cryosurgery probe may be substantially rigid for convenience of insertion inside the body. An exemplary cryosurgical probe is distributed by Endocare, Healtronics™ (Irvine, CA). Other exemplary cryosurgical probes are distributed by Galil Medical, BTG International (London, UK). The cryosurgical probe may have an outer diameter of between about 1.5 mm and 4.0 mm, for example, about 1.5 mm, about 1.7 mm, about 2.1 mm, about 2.4 mm, and about 3.8 mm. cryoprobes have diameters of 1.5 mm, 2.1 mm and 2.4 mm.

The cryosurgical probe may be formed of a biocompatible material. The cryosurgical probe may be formed of a material with mechanical properties that, at cryogenic temperatures, may withstand pressures which develop inside the cryosurgical probes. The breach of the cryosurgical probe inside the body can be fatal. The cryosurgical probe may be formed of a material which allows good heat transfer. In some embodiments, the cryosurgical probe may be formed of stainless steel. Exemplary materials include stainless steel #304 (0Cr18Ni9) and stainless steel #316 (0Cr17Ni12Mo2). The cryosurgical probe may be a single-use cryosurgical probe. The cryosurgical probe may be a multi-use cryosurgical probe. Multi-use cryosurgical probes may be coated with an inert coating selected to improve structural integrity of the cryosurgical probe against increased pressures. For example, multi-use cryosurgical probes may be coated in an inert gold coating.

The cryosurgery probe may be or include any part as described in U.S. Pat. Nos. 5,254,116; 5,334,181; 5,800,487; 5,800,488; 5,910,104; 6,475,212; 6,142,991; 6,179,831; 6,139,544; 5,513,742; 6,471,694; and 5,978,697, each of which is incorporated herein by reference in its entirety for all purposes.

The cryosurgical treatment may generally be sufficient to produce tissue ablation by freezing. Cryosurgical treatment may include bringing the target tissue to a temperature below the freezing temperature of biological tissues, typically −0.56° C. and lower. The effect of freezing the target tissue (whether preserving the biological matter or destroying it) may be controlled by selecting cooling rate during freezing and temperature. FIG. 2 illustrates the spatial temperature distribution during freezing of tissue 10, as a function of time after the onset of freezing. The cryosurgical probe surface 220 is at the origin. The temperature distribution in the ice ball 255 ranges from the temperature of the cryosurgical probe on the outer surface of the probe 255a (typically the coolest temperature of the treatment area), to the change of phase temperature at the outer margin of the frozen lesion in contact with the unfrozen tissue 255b (typically the warmest temperature of the treatment area).

In certain embodiments, cryosurgical treatment may be performed with intraoperative imaging, to monitor the extent of the frozen lesion in real time. The real time intraoperative imaging may be performed, for example, with a camera or sonogram.

FIG. 2 shows a schematic of the ice ball around a typical cryosurgery probe. Cryosurgery probe part 220 may experience a range of temperatures from about 0° C. to −40° C. The frozen tissue, sometimes referred to as the "ice ball" 255, may experience a range of temperatures from −40° C. to the phase transition temperature. Thus, a substantial portion of the frozen lesion may generally be between the 0° C. and −40° C. Therefore, while intraoperative medical imaging can generate a precise image of the outer margin of the frozen lesion, the extent of tissue ablation in that frozen region is typically unknown. Certain cells may survive temperatures up to about −20° C. By combining ablation methods, cell and tissue ablation may be improved. Other ablation methods may include, for example, electrolysis, electroporation (non-thermal irreversible electroporation and electrolytic electroporation), electrochemotherapy, radiofrequency, microwave, laser, and Joule heating. In particular, the cryosurgery instrument disclosed herein may combine cryogenic ablation with a non-thermal ablation method, such as electrolysis, electroporation (non-thermal irreversible electroporation and electrolytic electroporation), and electrochemotherapy, which is capable of generating products of electrolysis.

The cryosurgical instrument may comprise at least one electrode for conducting a current through a solution. The solution may be native to the target tissue and/or may be introduced to the target tissue. In some embodiments, the at least one electrode may be a treatment pad for surface treatments. In some embodiments, the at least one electrode may include needle electrodes and/or a catheter for use within cavities and/or tissues. In some embodiments, the electrode may be thermally conductive. The electrode may be formed of an electrically conductive material, for example, graphite, copper, silver, titanium, brass or an electrically conductive polymer such as a thermoplastic resin polymer. One exemplary thermoplastic resin polymer is used in CONDUCTOMER®. The electrode may be formed of carbon, titanium, or titanium coated with an oxide.

Systems and methods may comprise administering a solution for the electrolytic treatment. The solution may be an aqueous matrix administered in contact with the electrodes, proximate the target tissue. The aqueous matrix may be a biocompatible gel and/or a biocompatible solution, for example, a saline solution.

The electrode may be configured to generate products of electrolysis at the target tissue. Products of electrolysis may be generated by electrolysis. Electrolysis generally involves running an electrical current between two electrodes (a cathode and an anode) through an aqueous medium. At the cathode, positive ions are drawn to the electrode, which delivers electrons. At the anode, electrons are accepted. A potential drop associated with activation energy typically occurs across a boundary layer around the electrodes.

Biological tissue is an aqueous medium which may be treated with electrolysis. The electrical current may be sufficient to produce an electrochemical reaction at the electrodes in which electrons are transferred or received from the ions in the aqueous medium. The dose of electrical current may be sufficient to change the composition of the medium at the electrode boundary. In certain embodiments, the dose of electrical current may be sufficient to affect, through diffusion and electro-osmosis, the composition of the medium throughout a pre-selected volume of the medium.

Products of electrolysis may be generated to perform electrolytic ablation. In biological tissue, the products of electrolysis can be toxic to living cells. The extent of cell death generally depends on the composition of the electrodes and the composition of the solution. There are various parameters that may be used to control the products and outcome of the electrolytic process. The parameters include, for example, dosage, current, charge (i.e. period of time of delivery of current), pH, the type of electrode and catalysts for enhancing or reducing the products of electrolysis. In particular embodiments, current per surface area of electrodes per unit time may be selected to control the extent of ablation. In some embodiments, voltage may be selected to control the extent of ablation. The electrodes may be capable of applying a voltage from 0.5 V to 500 V. However, the activation potential is dependent on electrode material and composition. Time of the reaction may be selected to be on the order of seconds to hours. In general, the products of electrolysis may be generated substantially continuously or in pulses. The electrodes may be capable of applying a current between about 0.0001 $mA/cm^2$ electrode surface to 1000 $mA/cm^2$ electrode surface. The specific voltage, timing, and current may be selected based on the material of the electrode, the composition of the target tissue, and the desired or target amount of tissue/cell ablation.

Products of electrolysis may be generated by electroporation, for example, reversible and irreversible electroporation. Electroporation is the permeabilization of the cell membrane with electric fields delivered across the cell. Electroporation may be reversible. In reversible electroporation, generally the cell membrane recovers to the original permeability a certain time after the delivery of the pulses. Electroporation may be irreversible. In irreversible electroporation, generally the cell succumbs to the effects of the electric pulses. Both reversible and irreversible electroporation electric pulses may be designed to produce limited thermal damage. Thus, electroporation is typically considered a non-thermal method of ablation.

Any tissue ablation technique, for example, reversible electroporation, may be used for tissue ablation in combination with the administration of cytotoxic chemicals, such as bleomycin or cisplatin (cisplatinum). The cytotoxic chemicals may be administered, for example, injected, into or near the target tissue prior to the delivery of the electroporation electric pulses. Irreversible electroporation may be used for non-thermal tissue ablation. Irreversible electroporation tissue ablation may be done by applying electric fields between two electrodes bracing the targeted tissue.

Tissue ablation by irreversible electroporation may be performed by the methods described in U.S. Pat. No. 8,048,067, filed Oct. 18, 2006, titled "Tissue ablation with irreversible electroporation," incorporated by reference herein in its entirety for all purposes.

During electroporation, the electric field generated may also produce products of electrolysis. When purposefully generated in a controlled way, electrolysis can be used with electroporation in both the reversible and irreversible mode for tissue ablation. Thus, the methods disclosed herein may comprise generating products of electrolysis with electroporation. Electrolytic electroporation may include applying an electric field to permeabilize the cell membrane at a voltage and charge sufficient to generate products of electrolysis which contribute to the cell ablation.

Electrolytic electroporation may be performed by the methods described in U.S. Patent Application Publication No. 2016/0296,269, filed May 12, 2016, titled "Methods, systems, and apparatus for tissue ablation using electrolysis and permeabilization," incorporated herein by reference in its entirety for all purposes.

The cryosurgical instrument may be capable of performing cryoelectrolysis. Cryoelectrolysis may refer to combinations of treatment which produce products of electrolysis (purposefully or inadvertently) with cryosurgery/cooling. Such treatments may include cryosurgery-electrolysis, cryoelectroporation, cryoelectrolytic-electroporation, cold electrolysis, cold electroporation and coldelectrolytic electroporation.

As previously described, certain cells can survive cryosurgery in high subzero centigrade frozen tissue, from about −40° C. to the freezing interface. Non-thermal methods of tissue ablation, such as electroporation and electrolysis, may be combined with cryosurgery to ablate cells surviving cryosurgery, for example, without the injection of drugs into the treated tissue. Additionally, temperature may be used to modulate and control electric fields in biological tissues and can therefore be used to improve and control electrolytic treatments. Products of electrolysis may be delivered, before, during, and/or after the cryogenic treatment.

The methods disclosed herein may be used to provide combined cryosurgical treatment and electrolysis, for example, with a cryosurgical instrument as described herein. The methods may generally comprise bringing the cryosurgical instrument into contact with a target tissue and delivering a cryosurgical treatment to the target tissue. The cryosurgical treatment may include cooling the target tissue to a temperature between about 0° C. and −40° C. For instance, the cryosurgical treatment may be provided by cooling the cryosurgical probe to a temperature between about 0° C. and −40° C., for example, about −40° C., about −30° C., about −20° C., about −10° C., about −5° C., or about 0° C. The cryosurgical probe may cool the contacted target tissue to the selected temperature range. The target temperature may be selected to cause a maximum amount of ablation by cryogenic freezing of the cells, or the target temperature may be selected to be below a threshold of cell death.

The methods may additionally comprise generating products of electrolysis at the target tissue. The products of electrolysis may be generated by an electrical current of between about 0.0001 $mA/cm^2$ electrode surface to 1000 $mA/cm^2$ electrode surface, for example, between about 0.01 $mA/cm^2$ electrode surface to 1000 $mA/cm^2$ electrode surface, about 1 $mA/cm^2$ electrode surface to 500 $mA/cm^2$ electrode surface, or about 10 mA/cm² electrode surface to 200 mA/cm² electrode surface. The products of electrolysis may be generated by applying a voltage between about 0.5V and 500V, for example, between about 5V and 200V, or between about 5V and 50V. The applied current and voltage may be selected based on factors such as electrode material and composition of the target tissue. In general, the applied current and voltage may be selected to generate a predetermined amount of products of electrolysis. Specifically, the applied current and voltage may be selected to effectively ablate the target tissue when applied in combination with the cryosurgery.

The cryoelectrolysis may comprise providing the cryosurgical treatment and products of electrolysis such that each substantially simultaneously treats the target tissue. In some embodiments, a procedure that generates products of electrolysis may be followed by cryosurgery treatment. Electrolysis may deliver electrolysis products to the target tissue. Cells at the target tissue may have increased susceptibility to cell death due to the combined delivery of the electrolysis products and cryosurgery treatment. In some embodiments, electrolysis may be repeated after cryosurgical treatment. In some embodiments, electrolysis and cryosurgery may be performed at some time simultaneously. In some embodiments, electrolysis and cryosurgery treatment may be repeated in an alternating fashion for a desired period of time. Electrolysis and cryosurgery may be performed for the same or different time durations, magnitudes, and/or other parameters. In some embodiments, electrolysis and cryosurgery may be separated by a period of time where no treatment is applied to the target tissue.

In some embodiments, cryosurgery treatment may be performed and may be followed by electrolysis. Cells at the target tissue may have increased permeability in response to the cryosurgery. In some embodiments, cryosurgery may be repeated after electrolysis. In some embodiments, cryosurgery and electrolysis may be repeated in an alternating fashion for a desired period of time. Cryosurgery and electrolysis may be performed for the same or different time durations, magnitudes, and/or other parameters. In some embodiments, cryosurgery and electrolysis may be separated by a period of time where no treatment is applied to the target tissue.

In some embodiments, electrolysis and cryosurgery treatment may be performed at the same time or partially at the same time. For example, a current to generate electrolysis products may be applied during a same period of time as cryogenic temperatures are applied to the target tissue. In some embodiments, electrolysis and cryosurgery may both be performed together for a continuous period of time or intermittently. In some embodiments, one treatment may be performed continuously while the other treatment is performed intermittently. The magnitude and duration of each treatment may be modulated independently of the other treatment. For example, electrolysis may be performed for several seconds each minute, while cryosurgery treatment may be performed continuously for several minutes. The electrolysis may be discontinued while the cryosurgery treatment is continued. Such treatment combinations are exemplary. Other treatment protocols are within the scope of the disclosure. The time, duration, and order of the treatment may be selected based at least in part on the desired effect on the target tissue, the size of the target tissue, and/or local physiological conditions of the target tissue.

Each of the cryosurgical treatment and the electrolysis may be independently controlled. For example, dosage, timing, and magnitude of the cryosurgical treatment and the electrolysis may be independently controlled. The method may comprise providing one or both treatments continuously, intermittently, or periodically. The method may comprise providing one or both treatments at a substantially constant magnitude or by varying magnitude, for example, increasing or decreasing the applied treatment over time. The method may comprise providing one or both treatments at a substantially constant dosage or by varying dosage, for example, increasing or decreasing the dosage in subsequent treatments. The method may comprise administering an initial dosage of the cryosurgical treatment and/or the electrolysis. The method may comprise administering one or more bolus dosages of the cryosurgical treatment and/or the electrolysis. The method may comprise monitoring the target tissue to determine the course of treatment. In other embodiments, the course of treatment may be pre-selected. For example, the target tissue may be pre-cooled or cooled during the delivery of current to avoid carbonization, which may also avoid loss of conductivity.

The electric charge may be delivered in pulses (for example, as pulsed electric fields (PEF)). In some embodiments, the cryosurgical probe may simultaneously deliver pulsed electric fields and cooling temperatures. In such embodiments, the cryosurgical probe is electrically active and operates with the electrode. While not wishing to be bound by theory, it is believed that changes in electrical properties due to temperature produced by the pulsed protocol may magnify and confine electric fields in the cooled regions, while almost eliminating electric fields in surrounding regions. Simultaneous pulse protocols may be used to increase precision in the electrolytic procedure and reduce muscle contractions and damage to adjacent tissues. Additionally, electric pulses may induce blood flow stasis, which helps in reducing the heat load during cryosurgery.

In some embodiments, the cryosurgical probe may be substantially electrically inactive, and only apply cooling boundary conditions. In such embodiments, the cryosurgical instrument may comprise an electrode pair operating to produce the electrolytic effect. The temperature induced changes in the electrical properties of tissue may reduce the electric fields in the cooled regions. Cryoelectrolytic treatment may be used to protect sensitive tissues from the effect of the electric field.

During cryoelectrolysis, the dosage of cryogenic treatment and electrochemical current may be selected to treat an overlapping pre-selected volume of tissue. The pre-selected volume of tissue may be the target tissue. Thus, the target tissue includes a volume of tissue pre-selected for substantially simultaneous treatment by the cryosurgical probe and the products of electrolysis. The cryosurgical probe and the at least one electrode may be positioned and arranged to treat the target tissue. In some embodiments, the electrode may be fastened to the cryosurgical probe. In some embodiments, the electrode may be separate from the cryosurgical probe. In use, the cryosurgical probe may be placed proximately to the at least one electrode. In use, the cryosurgical probe may be placed at a pre-selected distance from the at least one electrode. The positioning may be selected based on the location and size of the target tissue.

The cryosurgical instrument may comprise an array of cryosurgical probes and electrodes. The at least one cryosurgical probe and the at least one electrode may be localized on the cryosurgical instrument in a variety of ways. In some embodiments, at least one electrode may be coupled and/or fastened to the cryosurgical probe. For example, at least one electrode may be coupled and/or fastened to a portion of the exterior surface of the cryosurgical probe. In some embodiments, at least one electrode may be dimensioned to conform to at least a portion of the exterior surface of the cryosurgical probe.

An electrode coupled to the cryosurgical probe may be movable along the exterior surface of the cryosurgical probe. For example, the positioning of the electrode on at least a portion of the exterior surface of the cryosurgical probe may be variable. In certain embodiments, the electrode may be expandable or contractable, such that the electrode may occupy a greater or smaller surface area on the surface of the cryosurgical probe.

The localization of the cryosurgical probe and the at least one electrode on the cryosurgical instrument may be fixed or variable. In some embodiments, coupled and/or fastened components may be removable, for example, reversibly removable. In some embodiments at least one electrode may be distinct from the cryosurgical probe. The distance between the cryosurgical probe and the distinct electrode may be fixed or variable. For example, the cryosurgical probe and/or the electrode may be rigidly positioned on the cryosurgical instrument or flexibly positioned. An electrode may be placed near the intended margin of the frozen lesion while the cryosurgery probe is placed at a site removed from the intended margin, which may promote cell death at or near the margin without reaching low subzero temperatures in the same region.

To provide products of electrolysis, the cryosurgical device may generally comprise an anode and a cathode. The at least one electrode may include at least one electrode which is electrically wired as an anode and at least one electrode which is electrically wired as a cathode. In some embodiments, the electrode may generate products of electrolysis by operating in conjunction with the cryosurgical probe. Thus, the cryosurgical probe may be electrically wired as the second electrode. In certain embodiments, the cryosurgical probe may be electrically wired as an anode. In certain embodiments, the cryosurgical probe may be electrically wired as a cathode.

However, the products of electrolysis effective to perform tissue ablation can cause damage to the cryosurgery probe. Corrosion to the material of the cryosurgical probe by products of electrolysis can be detrimental to the subject, in some instances, life threatening. The cryosurgical instrument disclosed herein may comprise a protective member coupled to at least a portion of an exterior surface of the cryosurgical probe. In embodiments which include more than one cryosurgical probe, at least one cryosurgical probe may comprise a protective member. The protective member may be effective to substantially isolate the cryosurgical probe from the products of electrolysis. In some embodiments, the protective member may be effective to completely isolate the cryosurgical probe from the products of electrolysis.

The protective member may be thermally conductive. For instance, the protective member may substantially isolate the cryosurgical probe from products of electrolysis, while maintaining thermal treatment of the target tissue. The protective member may not substantially interfere with the heat transfer between the target tissue and the cryosurgical probe. Furthermore, the protective member may not substantially interfere with the electrolytic treatment at the target tissue.

The protective member may be dimensioned to effectively substantially isolate the cryosurgical probe from the products of electrolysis. For example, the protective member may have a thickness effective to substantially isolate the cryosurgical probe from the products of electrolysis when conformed to the cryosurgical probe. The protective member may have a thickness of between about 0.001 mm to about 5.0 mm, for example, between about 0.01 mm to about 3.0 mm or between about 0.1 mm to about 2.0 mm, when conformed to the cryosurgical probe, i.e. from an interior surface of the protective member facing and/or contacting the cryosurgical probe to an exterior surface of the protective member facing and/or contacting the target tissue. The effective dimensions to substantially isolate the cryosurgical probe from the products of electrolysis may be dependent on the material of the protective member and the amount of products of electrolysis (which may be dependent on the composition of the target tissue and the electrolysis dosage).

The protective member may be formed of a material effective to substantially isolate the cryosurgical probe from the products of electrolysis. For example, the material of the protective member may be effective to substantially isolate the cryosurgical probe from the products of electrolysis when provided at the effective dimensions (described above). The effective material to substantially isolate the cryosurgical probe from the products of electrolysis may be dependent on the dimensions of the protective member and the amount of products of electrolysis (which may be dependent on the composition of the target tissue and the electrolysis dosage).

The protective member may be in the form of a metallic coating on the cryosurgical probe. The metallic coating may be fixed or removable. The metallic coating may provide galvanic protection to the cryosurgical probe material when exposed to products of electrolysis. In some embodiments, the material of the protective member may be more anodic than the material of the cryosurgical probe. Table 1 includes a list of metallic materials, from most active (more anodic) to least active (less anodic). The protective member may be formed of a material higher up in Table 1 from the material of the cryosurgical probe. Materials on the same line of the table are substantially equally anodic.

TABLE 1

| Cryosurgical Probe and Protective Member Materials, Most Anodic to Least Anodic | | | | | | |
|---|---|---|---|---|---|---|
| Magnesium alloys | — | — | — | — | — | — |
| Zinc | — | — | — | — | — | — |
| Beryllium | — | — | — | — | — | — |
| Aluminum 1100 | Aluminum 3003 | Aluminum 3004 | Aluminum 5052 | Aluminum 6053 | — | — |
| Galvanized steel | — | — | — | — | — | — |
| Cadmium | — | — | — | — | — | — |
| Aluminum 2017 | Aluminum 2024 | Aluminum 2117 | — | — | — | — |

TABLE 1-continued

Cryosurgical Probe and Protective Member Materials, Most Anodic to Least Anodic

| | | | | | | |
|---|---|---|---|---|---|---|
| Mild steel 1018 | Wrought iron | — | — | — | — | — |
| Cast iron | Low alloy high strength steel | — | — | — | — | — |
| Chrome iron (active) | — | — | — | — | — | — |
| Stainless steel 430 series (active) | — | — | — | — | — | — |
| Stainless steel 302 (active) | Stainless steel 303 (active) | Stainless steel 304 (active) | Stainless steel 321 (active) | Stainless steel 347 (active) | Stainless steel 410 (active) | Stainless steel 416 (active) |
| Nickel (resist) | — | — | — | — | — | — |
| Stainless steel 316 (active) | Stainless steel 317 (active) | — | — | — | — | — |
| Carpenter 20 CB-3 stainless (active) | — | — | — | — | — | — |
| Aluminum bronze (CA 687) | — | — | — | — | — | — |
| Hastelloy C (active) | Inconel 625 (active) | Titanium (active) | — | — | — | — |
| Lead-tin solders | — | — | — | — | — | — |
| Lead | — | — | — | — | — | — |
| Tin | — | — | — | — | — | — |
| Inconel 600 (active) | — | — | — | — | — | — |
| Nickel (active) | — | — | — | — | — | — |
| Brass (naval) | Brass (yellow) | Brass (red) | Brass (admiralty) | — | — | — |
| Copper (CA 102) | — | — | — | — | — | — |
| Manganese bronze | Manganese tin | — | — | — | — | — |
| Silicon bronze | — | — | — | — | — | — |
| Nickel silver | — | — | — | — | — | — |
| Copper-nickel alloy | — | — | — | — | — | — |
| Stainless steel 430 | — | — | — | — | — | — |
| Nickel (passive) | Aluminum | Bronze | — | — | — | — |
| Monel 400 | K 50 | — | — | — | — | — |
| Silver solder | — | — | — | — | — | — |
| Nickel (passive) | — | — | — | — | — | — |
| Chrome iron (passive) | — | — | — | — | — | — |
| Stainless steel 302 (passive) | Stainless steel 303 (passive) | Stainless steel 304 (passive) | Stainless steel 421 (passive) | Stainless steel 347 (passive) | — | — |
| Stainless steel 316 (passive) | Stainless steel 317 (passive) | — | — | — | — | — |
| Carpenter 20 CB-3 stainless (passive) | Incoloy 825 | — | — | — | — | — |
| Nickel Molybdenum chromium iron alloy (passive) | — | — | — | — | — | — |
| Silver | — | — | — | — | — | — |
| Titanium | Titanium alloys | — | — | — | — | — |
| Graphite | — | — | — | — | — | — |

TABLE 1-continued

Cryosurgical Probe and Protective Member Materials, Most Anodic to Least Anodic

| | | | | | | |
|---|---|---|---|---|---|---|
| Zirconium | — | — | — | — | — | — |
| Gold | — | — | — | — | — | — |
| Platinum | — | — | — | — | — | — |

The protective member may be a sacrificial member. In use, the products of electrolysis may cause corrosion of the more anodic sacrificial material. However, the extent to which a sacrificial protective coating can continue to protect the cryogenic probe is directly related to the thickness of the protective member, because the protective member may wear out with use. Thus, in some embodiments, the protective member may have a thickness effective to withstand a cryoelectrolysis treatment. The protective member may be a single-use device. The protective member may be a non-sacrificial coating. For example, the protective member may be formed of platinum or a polymer (conductive or non-conductive polymer).

The protective member may be non-electrically conductive. For example, the protective member may be formed of a non-electrically conductive plastic, such as teflon. In some embodiments, the protective member may be electrically insulating or may comprise an electrically insulating layer. ANSI standards, for example, ANSI C33.60 may be used for the electrical insulation material. The material of the protective member may be thin, so as not to interfere with heat transfer from the cryosurgical probe.

The protective member may be substantially free of impurities and formed with a robust material. It is noted that if the cryogenic probe becomes exposed through an impurity in the protective member, the cryogenic probe material may corrode when contacted with the products of electrolysis.

In some embodiments, the protective member may be movable along the exterior surface of the cryosurgical probe. For example, the positioning of the protective member on at least a portion of the exterior surface of the cryosurgical probe may be variable. In certain embodiments, the protective member may be expandable or contractable, such that the protective member may occupy a greater or smaller surface area on the surface of the cryosurgical probe.

The protective member may be removable, for example, reversibly removable, from the cryosurgical instrument. Thus, a cryosurgical probe protective device is disclosed herein. The protective device may be dimensioned to conform to at least a portion of an exterior surface of the cryosurgical probe. The protective device may be malleable or substantially rigid. The protective device may be provided in a sealed container. For example, the protective device may be provided in sterile packaging. The protective device may be individually wrapped. The protective device may be a single-use device. The protective device may be a multi-use device.

In some embodiments, the protective member may be formed as a single piece with the electrode. Thus, the protective device may comprise an electrode portion adjacent to the protective portion. When assembled, the electrode may be coupled to a portion of the exterior surface of the cryosurgical probe adjacent to the protective member.

A kit comprising the protective device (as previously described) and instructions for use is also disclosed. The instructions may instruct a user to apply the protective device to the cryosurgical probe. The instructions may instruct the user to fasten the protective device to the cryosurgical probe. In some embodiments, the instructions may provide one or more parameter for the cryoelectrolytic treatment, for example, a minimum temperature or maximum electrical charge which may be applied to the protective device without causing substantial damage to the protective device.

The cryosurgical instrument may further comprise a vacuum layer between the exterior surface of the cryosurgical probe and the protective member. In some embodiments, the vacuum layer may be movable along the exterior surface of the cryosurgical probe. For example, the vacuum layer may be movable along the exterior surface of the cryosurgical probe independently from any mobility of the protective member. The vacuum layer may have a thickness of between about 0.01 mm to about 5.0 mm, for example, between about 0.1 mm to about 2.0 mm. In some embodiments, the cryosurgical instrument may comprise a heat transfer fluid between the cryosurgical probe and the protective member.

The cryosurgical instrument may be part of a system for performing cryoelectrolysis. In addition to the cryosurgical instrument, the system may include a cryogenic power supply electrically connected to the cryosurgical probe, an electrolysis power supply electrically connected to the at least one electrode, and a controller. The system may additionally include one or more sensors configured to measure a parameter of the target tissue and provide feedback information to the controller.

Methods of producing a cryosurgical instrument are also disclosed. The methods may comprise selecting a cryosurgical probe and selecting an electrode. In certain embodiments, the methods may comprise selecting an arrangement for the cryosurgical probe and electrode, and, optionally, coupling and/or fastening the electrode to the cryosurgical probe. The methods may comprise coupling and/or fastening a protective member or device to the cryosurgical probe. For example, the methods may comprise coupling and/or fastening a protective member or device to at least a portion of an exterior surface of the cryosurgical probe. In certain embodiments, the methods may comprise positioning a vacuum layer between the external surface of the cryosurgical probe and the protective member.

The methods of producing a cryosurgical instrument may comprise selecting materials for one or more of the cryosurgical probe, the electrode, and the protective member. Properties which may be considered when selecting the materials include, for example, electrical conductivity, thermal conductivity, corrosion resistance, hardness, and form.

As disclosed herein, "electrical conductivity" refers to a material's ability to carry or conduct an electric current. Electrical conductivity may be reported as a percent of the copper standard, 100% IACS (International Annealed Copper Standard). As an exemplary embodiment, silver has an IACS of 105%.

As disclosed herein, "thermal conductivity" refers to a material's ability to carry or conduct heat. As an exemplary embodiment, gold is a material with high thermal conductivity.

As disclosed herein, "corrosion resistance" is a material's ability to resist chemical decay. A material that has little corrosion resistance will degrade rapidly in corrosive environments, resulting in a shorter lifespan. As an exemplary embodiment, platinum group metals are known for high resistance to corrosion. Polymer materials such as teflon are generally resistant to corrosion.

As disclosed herein, "hardness and elasticity" is the measure of how resistant the material is to various kinds of permanent deformations resulting from an applied force. Hardness is generally dependent on a material's ductility, elasticity, plasticity, tensile strength, and toughness. In particular, hardness may be considered in the design of the protective member, as the insertion of a cryosurgical instrument in hard tissue is associated with substantial stresses and deformations.

As disclosed herein, "form" may generally refer to the shape an electrical material must fit in order to carry out its operation. Exemplary shapes include contact tips, pins, sockets, stampings, sheets, wires, and wheels.

The methods may comprise selecting a material for the protective member which facilitates the isolation of the cryosurgical probe from a potential electrolytic environment. The protective member may be formed of a material which has low electrical conductivity and high corrosion resistance.

The methods may comprise selecting a material for the protective member which does not substantially interfere with the removal of heat from the target tissue by the cryosurgical probe. The protective member may be formed of a material which has good thermal conductivity near the cooling part of the cryosurgical probe. Good thermal conductivity may be achievable by selecting a material with good thermal conductivity or selecting a thin form of a material with lower thermal conductivity.

The methods may comprise selecting a material for the protective member which does not substantially interfere with the electrolytic process in the target tissue. The protective member may be formed of a material which has a high electrical conductivity and a high corrosion resistance.

The methods may comprise selecting a material for the protective member which is substantially biocompatible. For sufficient biocompatibility, the material may be selected such that the products of electrolysis have a safe reaction with the material. Exemplary materials include carbon. In other embodiments, the material may be selected such that the products of electrolysis have a reaction with the material which contributes to tissue ablation. Exemplary materials include silver and copper. The methods may comprise selecting a material which has a sufficient hardness and elasticity to be compatible with the function of a cryosurgical probe.

The methods may comprise selecting a material for the protective member to be thermally conductive. The methods may comprise selecting a material for the protective member to be more anodic than a material of the cryosurgical probe. The methods may comprise selecting a material for the protective member and/or electrode from stainless steel, lead, gold, silver, copper, graphite, carbon, titanium, brass, bronze, platinum, palladium, mixed metal oxides, nickel, polymers (for example, nylon or polyolefin), composites thereof (for example, composites of conductive materials and insulative materials such as pyralux distributed by DuPont, Wilmington, DE, which is a composite of copper and polymer), and alloys thereof (for example, copper alloys with graphite, tellurium, and tungsten).

In an exemplary embodiment, the methods may comprise selecting copper as a material for the electrode and/or protective member. Copper ions are toxic to cells. The use of a protective member comprising copper may be desirable to enhance cell ablation. Alternatively, the use of a protective member comprising copper may not be desirable because of toxicity to tissue.

In an exemplary embodiment, the methods may comprise selecting graphite and/or carbon as a material for the electrode and/or protective member. Carbon is very inter-corrosion resistant, and electrochemically noble compared to many metals, which makes carbon a useful material for electrochemical and electrowinning electrodes. One drawback of carbon is the hardness and lack of elasticity.

In an exemplary embodiment, the methods may comprise selecting titanium or titanium oxide as a material for the electrode and/or protective member. Titanium has excellent corrosion properties. A thin layer of titanium or titanium oxide may be provided either through machining or electrodeposition.

In an exemplary embodiment, the methods may comprise selecting silver as a material for the electrode and/or protective member. Silver has high conductivity, softness (low hardness), and high resistance to oxidation. Silver may be strengthened with copper and other alloy additions, but at the sacrifice of conductivity. Silver may be selected in the form of Ag/AgCl. Silver ions are toxic to cells. The use of a protective member comprising silver may be desirable to enhance cell ablation. Alternatively, the use of a protective member comprising silver may not be desirable because of toxicity to tissue.

In an exemplary embodiment, the methods may comprise selecting platinum and/or palladium as a material for the electrode and/or protective member. Platinum and palladium have very high erosion and corrosion resistance with low contact resistance. Platinum may be used as an alloy with iridium, ruthenium, and/or tungsten. Palladium may be used as an alloy with copper and/or ruthenium.

The electrode and/or protective member material may comprise mixed metal oxides (MMO), for example, as a coating. Electrodes may typically have an oxide coating over an inert metal or carbon core. The oxides may include precious metal (for example, ruthenium, iridium, and platinum) oxides for catalyzing an electrolysis reaction. Dimensionally stable anodes may include a titanium base, coated with a very thin layer of mixed metal oxides. Titanium oxides may be used for inertness, electrode corrosion protection, and lower cost. Ruthenium and iridium oxides can be deposited on titanium, providing a catalytic effect to enhance the electrolytic reaction and promote the formation of hypochlorous acid, a chemical species that is effective at ablating cells and also used by the T-cells for cell ablation.

FIG. 1 is a schematic illustration of a system 100 including a cryosurgical instrument 125. The system 100 may be capable of performing both cryosurgery and an electrolysis product generating process. As shown in FIG. 1, the cryosurgical instrument 125 may be used on the surface of a target tissue 10, within the target tissue 10, proximate the target tissue 10, and/or in a cavity formed by the target tissue 10.

Exemplary system 100 includes controller 105. The controller 105 is operatively connected to the electrolysis power supply 110 and the cryogenic power supply 115, each of which is electrically connected to the cryosurgical instrument 125. The electrolysis power supply 110 and the cryogenic power supply 115 are shown as distinct devices in FIG. 1. However, the electrolysis power supply 110 and the cryogenic power supply 115 may be the same device. When in use, power supplies 110, 115 may be placed proximate to the treatment site or remotely from the treatment site. The system 100 may include a source of an aqueous solution (not shown) for administration to the target tissue. The aqueous solution may be effective to enhance the electrolytic treatment.

The controller 105 may be configured to control one or more parameter of the treatment. For example, the controller 105 may be configured to control at least one of dosage, timing, and magnitude of the cryosurgical treatment and the electrolysis. In general, the controller 105 may be configured to control the parameters for the cryosurgical treatment independently from the parameters of the electrolysis. The controller 105 may be configured to control the at least one parameter by instructing the power supplies 110, 115. For example, the controller 105 may be programmable to provide an generate an electric signal and to generate a cryogenic signal. The signals may be delivered to the power supplies 110, 115, respectively. The controller 105 may allow a user to customize treatment.

In some embodiments, a feedback system may be included in a communication path between the controller 105 and the cryosurgical instrument 125. System 100 may include one or more sensors 150 positioned to measure a property at the target tissue 10. The sensor 150 may be positioned on the cryosurgical instrument 125 or remotely from the cryosurgical instrument 125. The parameter may be, for example, temperature, pH, or electric field strength. Thus, the sensor 150 may be, for example, a temperature sensor, an electric current sensor, an electric potential sensor, a pH sensor.

Systems and methods disclosed herein may comprise measuring pH at the target tissue, for example, with sensor 150, during treatment, prior to treatment, and/or after treatment. The method may comprise providing or altering electrolysis responsive to the measured pH value. The method may comprise providing a pH adjusting agent to alter or control pH at the target tissue. The controller 105 may be configured to generate or modify the electric signal responsive to the pH measurement obtained by the sensor 150.

In exemplary embodiments, the pH sensor 150 may sense pH near the electrode and transmit the pH value to the controller 105. The controller 105 may be programmed to adjust an electric signal provided to the electrode based on the pH value near the electrode. A source of a pH adjusting agent (not shown) may be provided to store and deliver pH adjusting agent, for example, buffers or other solutions, to the target tissue.

In another exemplary embodiment, the pH sensor 150 may be positioned to measure pH at the outer edge of the target tissue. The pH sensor 150 may detect when the pH level at the target tissue edge has reached a pre-selected level, which may help ensure tissue ablation at the edge and throughout the target site. Detection of a desired pH level may be a prompt for the controller 105 to terminate electrolysis.

In another exemplary embodiment, the pH sensor 150 may be positioned at a selected target site and may detect pH level at the site as pH is reaching or has reached an undesirable value. Detection of a given pH value may be a prompt for the controller 105 to terminate electrolysis, which may help avoid tissue damage.

The controller 105 may be programmed to control pH near an anode to be between 6.5 and 2.5, for example, between 4.5 and 2.5. The controller 105 may be programmed to control pH near a cathode to be between 7.5 and 11, for example, between 8 and 10. The controller 105 may control pH by adjusting electric signal and/or instructing the source of pH adjusting agent to deliver a pre-determined amount of the pH adjusting agent. Thus, the controller 105 may be operatively connected to the source of pH adjusting agent.

Systems and methods disclosed herein may comprise measuring electric field strength (for example, electric current and/or electric potential) at the target tissue, for example, with sensor 150, during treatment, prior to treatment, and/or after treatment. The method may comprise providing or altering electrolysis responsive to the measured electric field strength value. The controller 105 may be configured to generate or modify the electric signal responsive to the electric field strength measurement obtained by the sensor 150.

Systems and methods disclosed herein may comprise measuring temperature at the target tissue, for example, with sensor 150, during treatment, prior to treatment, and/or after treatment. The method may comprise providing or altering the cryosurgical treatment responsive to the measured temperature value. The controller 105 may be configured to generate or modify the cryogenic signal responsive to the temperature measurement obtained by the sensor 150.

The controller 105 may be a separate component coupled to the power sources 110, 115, as shown in FIG. 1, or the controller 105 may be integrated into one or both power sources 110, 115, or packaged together with one or both power sources 110, 115. In some embodiments, the controller 105 may include a programmable chip coupled to the power sources 110, 115. In some embodiments, the controller 105 may be implemented using a computing device (not shown) and may be remotely coupled to the devices 110, 115. The computing device may be, for example, a desktop computer, laptop computer, server, cloud-based server, handheld computing device, tablet computer, and/or a smart phone. In some examples, the computing device may be integrated with and/or shared with a separate piece of medical equipment. The controller 105 may be coupled by a wire to the devices 110, 115 or may communicate with the devices 110, 115 wirelessly. In some embodiments, two separate controllers 105 may be used in the system 100. Each controller 105 may be coupled separately to one of the power sources 110, 115. Multiple controllers 105 may be coupled separately to one or more sensors 150.

The controller 105 may include a memory storage device or be coupled to a server or cloud computing system with memory storage. The controller 105 may, for example, include such a program, or include one or more processing devices (e.g. processors) coupled to the memory encoded with executable instructions for electrolysis treatment or cryosurgical treatment. The controller 105 may include an input device, for example, a keyboard, mouse, trackpad, or touch pad, and an output device, for example, a screen or speaker. The controller 105 may be programmed to operate with a mobile application and/or transmit notifications to a handheld computing device.

The systems described herein may additionally comprise one or more pumps, valves, and lines to carry out the functions described above. The system may be electrically connected to a power source and/or battery. The system may be stationary or portable.

Figure 3:
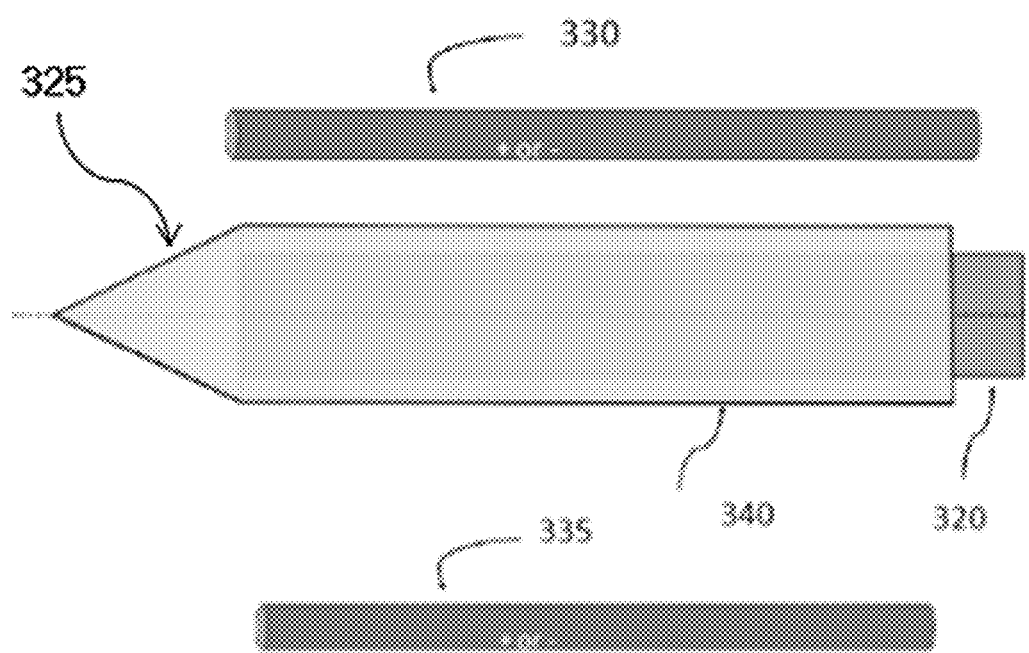
FIG. 3 is a schematic diagram of a cryosurgical instrument, according to one embodiment.

FIGS. 3-11 are schematic drawings of different cryosurgical instruments. FIG. 3 is a schematic drawing of a cryosurgical instrument 325 comprising a cryosurgical probe 320, protective member 340 covering a portion of the exterior surface of the cryosurgical probe 320, and electrodes 330, 335. Electrode 330 may be wired as the anode for electrolysis treatment. Electrode 335 may be wired as the cathode for electrolysis treatment. Protective member 340 may substantially isolate cryosurgical probe 320 from the products of electrolysis generated by electrodes 330, 335. In some embodiments, protective member 340 may be electrically insulating.

Figure 4:
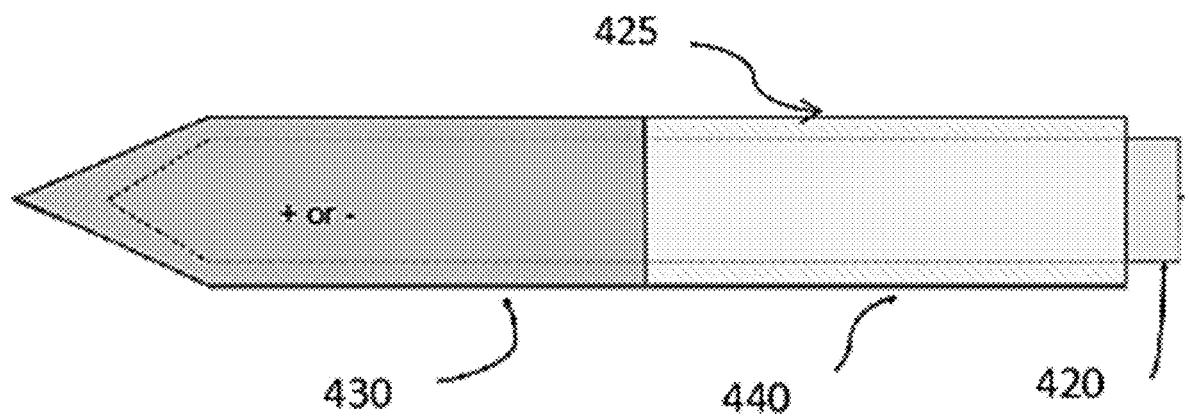
FIG. 4 is a schematic diagram of a cryosurgical instrument, according to an alternate embodiment.

FIG. 4 is a schematic drawing of an alternate cryosurgical instrument 425. Cryosurgical probe 420 is covered with an integral protective member 440 and electrode 430 device. The protective member 440 and electrode 430 have different thermal and electrical properties. Protective member 440 is formed as a sleeve around the cryosurgical probe 420 that is made of electrically insulative materials. Protective member 440 can also have thermal insulative properties. Electrode 430 is formed of a material which is both electrically and thermally conductive.

The electrical charge to the electrode 430 can be delivered either by connecting the electrode 430 directly to the power supply or connecting an electrically conductive cryosurgical probe 420 to the power supply. Either connection may result in an electrical charge on the outer surface of the electrode 430, in contact with the target tissue. In such a configuration, the electrode 430 may be in good thermal and electrical contact with the cryosurgical probe 420. Adequate thermal and electrical contact can be achieved by good mechanical contact between part 430 and 420 or the use of a thermal connective fluid or gel, such as THERM-A-GAP GEL (distributed by Parker Chomerics, Woburn, MA), Cool-Therm® MG-122 (distributed by LORD Corp., Cary, NC), or solutions of graphite.

Figure 5:
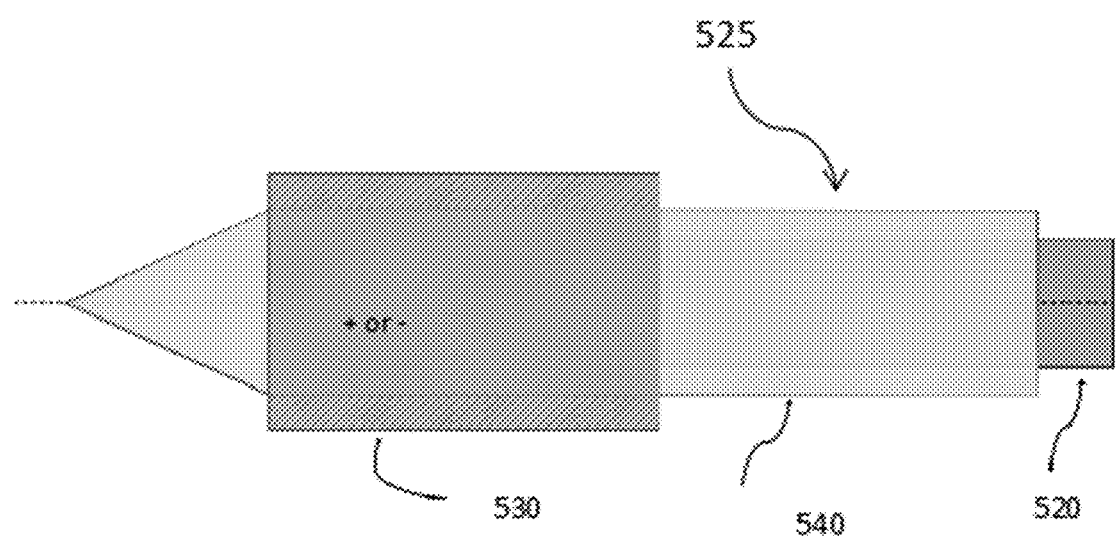
FIG. 5 is a schematic diagram of a cryosurgical instrument, according to an alternate embodiment.

FIG. 5 is a schematic drawing of another exemplary cryosurgical instrument 525. Cryosurgical instrument 525 includes cryosurgical probe 520. Protective member 540 is coupled to cryosurgical probe 520. In the exemplary embodiment of FIG. 5, the entire cryosurgical probe 520 is covered by protective member 540. Protective member 540 may be an electrically insulative material. Electrode 530 is coupled to protective member 540, covering a portion of protective member 540. In some embodiments, electrode 530 is movable along protective member 540.

Figure 6:
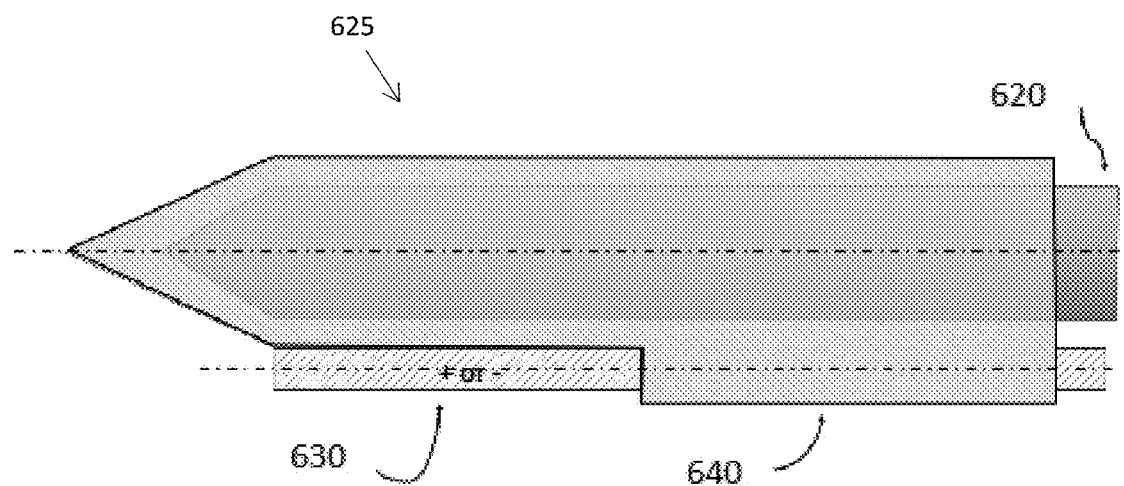
FIG. 6 is a schematic diagram of a cryosurgical instrument, according to an alternate embodiment.

FIG. 6 is a schematic drawing of another exemplary cryosurgical instrument 625. Cryosurgical instrument 625 includes cryosurgical probe 620. Protective member 640 is coupled to cryosurgical probe 620. In the exemplary embodiment of FIG. 6, the entire cryosurgical probe 620 is covered by protective member 640. Electrode 630 is fastened to the cryosurgical instrument 626 adjacent to the cryosurgical probe 620. Electrode 630 may be a cylindrical electrically conductive material. Electrode 630 is fastened to the instrument by an extension of the protective member 640. Electrode 630 is also covered with a portion of the protective member 640. Protective member 640 may be electrically insulative, to target or direct delivery of the electrical charge at a desired location. Electrode 630 may be near the cryosurgical probe 620 or at a greater distance from the cryosurgical probe 620.

Figure 7:
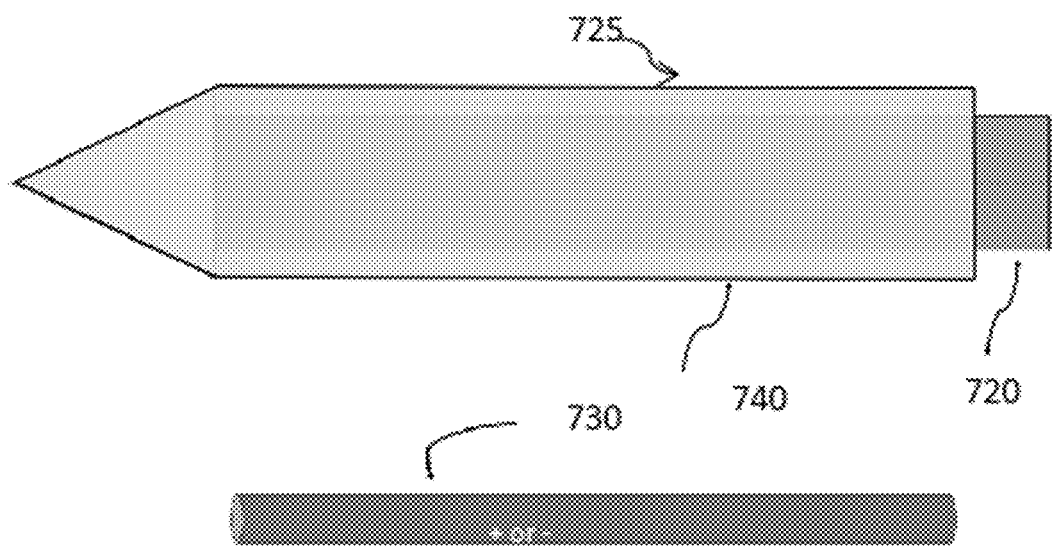
FIG. 7 is a schematic diagram of a cryosurgical instrument, according to an alternate embodiment.

FIG. 7 is a schematic drawing of another exemplary cryosurgical instrument 725. Cryosurgical instrument 725 includes cryosurgical probe 720. Protective member 740 is coupled to cryosurgical probe 720. In the exemplary embodiment of FIG. 7, the entire cryosurgical probe 720 is covered by protective member 740. Electrode 730 is not fastened to the cryosurgical probe 720. Instead, electrode 730 is separate from the cryosurgical probe 720 and protective member 740 arrangement.

Figure 8A:
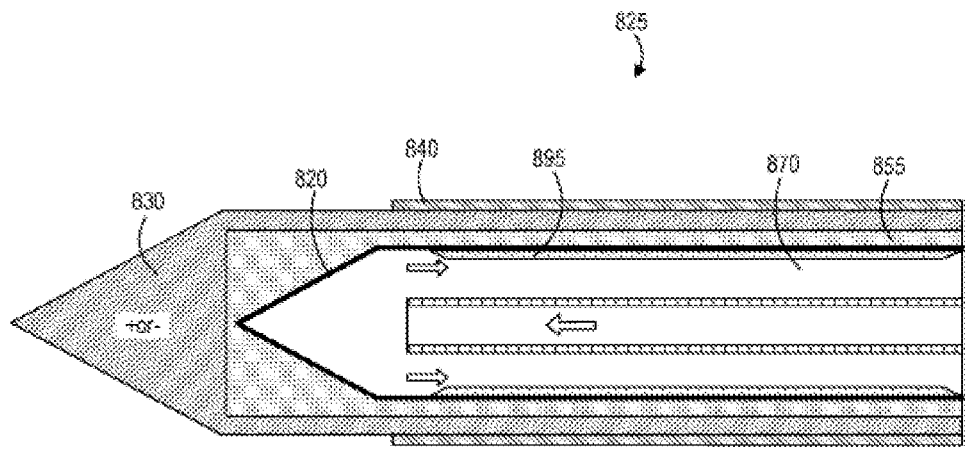
FIG. 8A is a schematic diagram of a cryosurgical instrument, according to an alternate embodiment.

FIG. 8A is a schematic drawing of another exemplary cryosurgical instrument 825. Cryosurgical instrument 825 includes cryosurgical probe 820 and electrode 830. Protective member 840 is coupled to cryosurgical probe 820 on an exterior surface of the electrode 830. Protective member 840 may be formed of a dielectric material, for example, parylene or teflon, for electrical insulation. Cryosurgical instrument 825 includes vacuum layer 895 which provides a gas insulation effect. Cryosurgical probe 820 includes channel 870 for circulation of the cooling fluid. Cryosurgical instrument 825 includes channel 855 for heat transfer fluid.

Figure 8B:
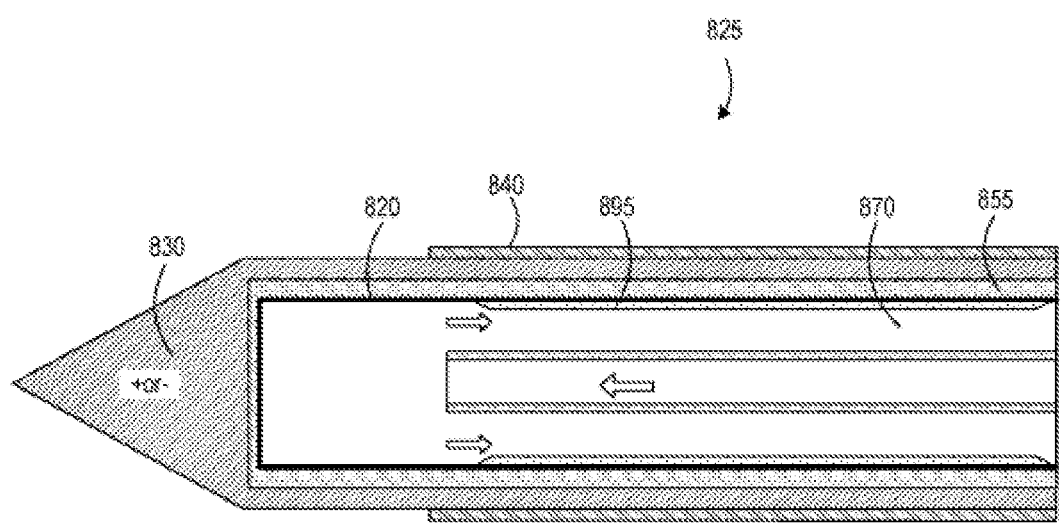
FIG. 8B is a schematic diagram of an alternate embodiment of the cryosurgical instrument of FIG. 8A.

FIG. 8B is a schematic drawing of an alternate configuration of exemplary cryosurgical instrument 825 as shown in FIG. 8A. The embodiment of cryosurgical instrument 825 of FIG. 8B is the same as cryosurgical instrument 825 of FIG. 8A, except the cryosurgical probe 820 has a blunt tip.

Figure 9:
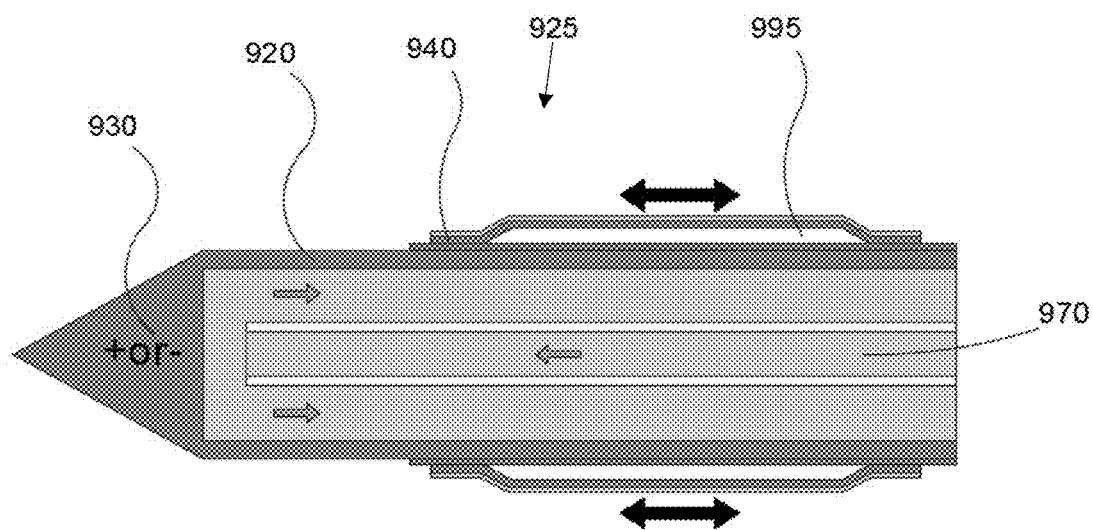
FIG. 9 is a schematic diagram of a cryosurgical instrument, according to an alternate embodiment.

FIG. 9 is a schematic drawing of another exemplary cryosurgical instrument 925. Cryosurgical instrument 925 includes cryosurgical probe 920 and electrode 930. Protective member 940 is coupled to cryosurgical probe 920 on an exterior surface of the vacuum layer 995. Vacuum layer 995 is positioned within protective member 940 on an exterior surface of the electrode 930. Protective member 940 is movable along cryosurgical instrument 925 to provide variable length heat insulation. The variable length heat insulation may be used to select a size of the ice balls. Cryosurgical probe 920 includes channel 970 for circulation of the cooling fluid.

Figure 10:
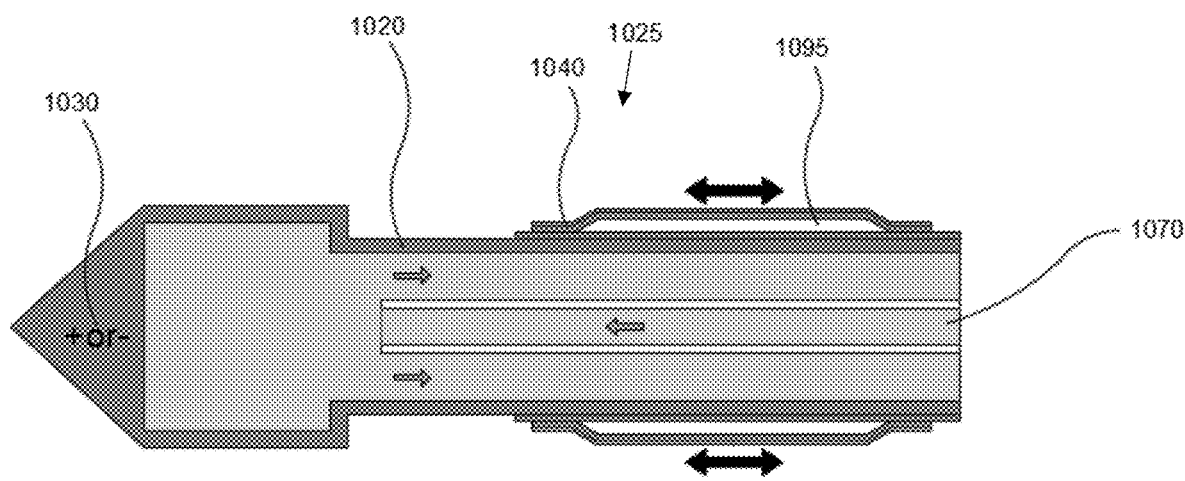
FIG. 10 is a schematic diagram of a cryosurgical instrument, according to an alternate embodiment.

FIG. 10 is a schematic drawing of another exemplary cryosurgical instrument 1025. Cryosurgical instrument 1025 includes cryosurgical probe 1020 and electrode 1030. Protective member 1040 is coupled to cryosurgical probe 1020 on an exterior surface of the vacuum layer 1095. Vacuum layer 1095 is positioned within protective member 1040 on an exterior surface of the electrode 1030. Protective member 1040 is movable along cryosurgical instrument 1025 to provide variable length heat insulation. The larger tip of the cryosurgical probe 1020 may be used to produce larger ice balls than, for example, the embodiment of FIG. 9. Cryosurgical probe 1020 includes channel 1070 for circulation of the cooling fluid.

Figure 11:
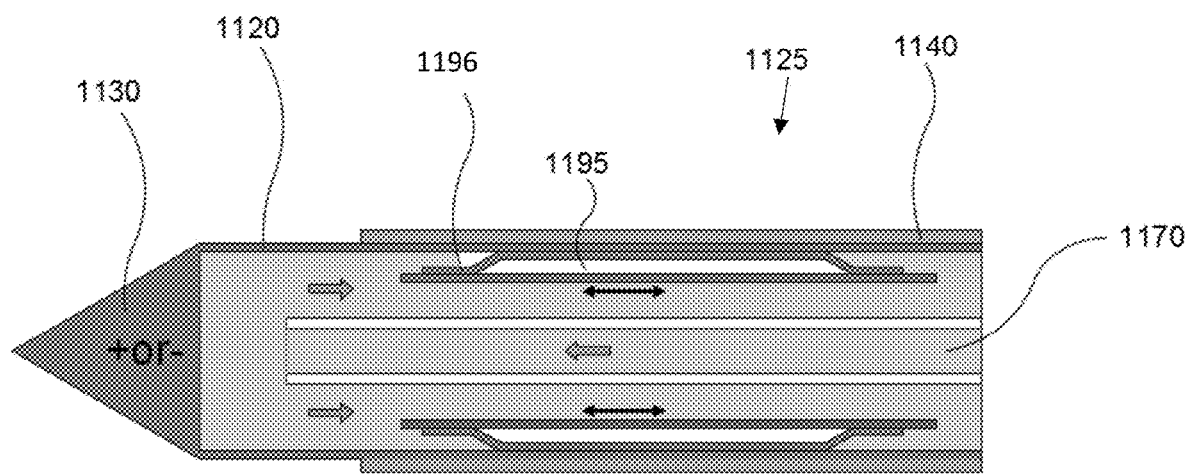
FIG. 11 is a schematic diagram of a cryosurgical instrument, according to an alternate embodiment.

FIG. 11 is a schematic drawing of another exemplary cryosurgical instrument 1125. Cryosurgical instrument 1125 includes cryosurgical probe 1120 and electrode 1130. Protective member 1140 is coupled to cryosurgical probe 1120 on an exterior surface of the electrode 1130. Vacuum layer 1195 is positioned within vacuum sleeve 1196 on an interior surface of the electrode 1130. Interior vacuum sleeve 1196 is movable along cryosurgical probe 1120 to provide variable length heat insulation. The variable length heat insulation may be used to select a size of the ice balls. Cryosurgical probe 1120 includes channel 1170 for circulation of the cooling fluid.

Figure 12:
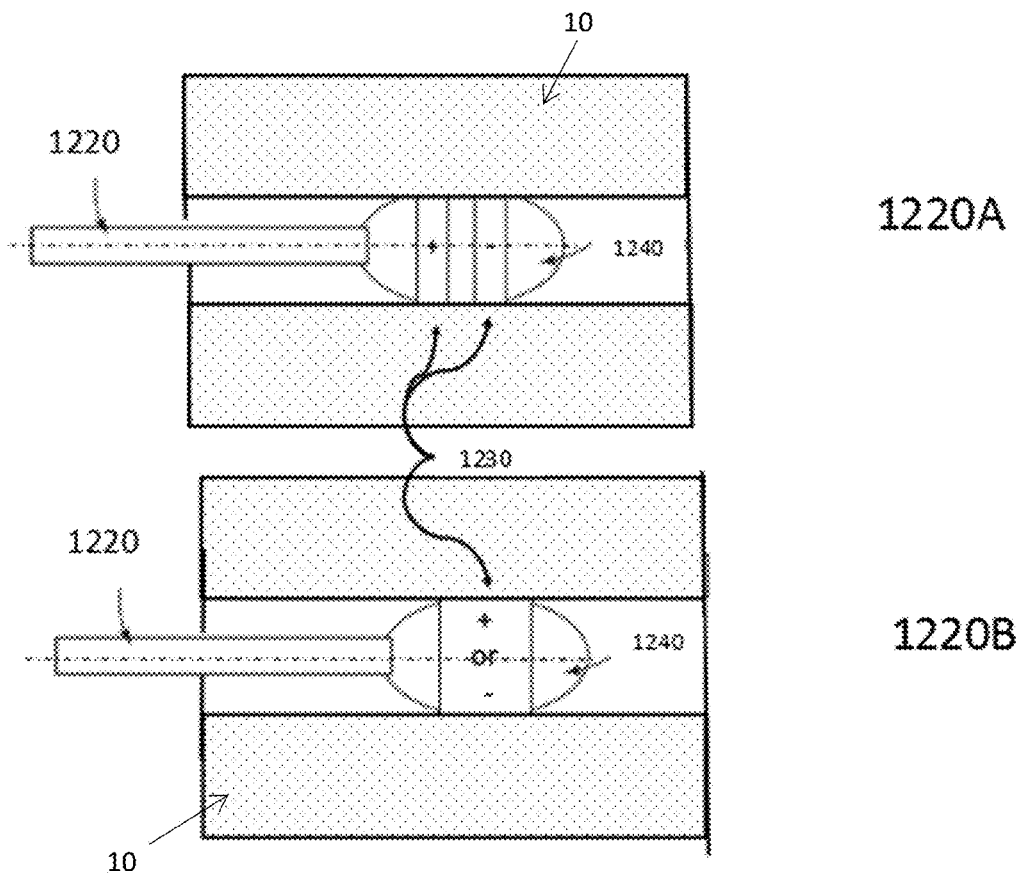
FIG. 12 is a schematic diagram of exemplary cryosurgical instruments in use, according to one embodiment.

FIG. 12 includes schematic drawings of cryosurgical instruments 1200A and 1200B in use treating tissue 10. Cryosurgical instruments 1200A-1200B are inserted in a target tissue cavity. The figure shows cross sections through the cavity in the target tissue 10. Cryosurgical probe 1220 includes protective member 1240 at a distal end. Electrodes 1230 are arranged slightly differently in cryosurgical instruments 1200A and 1200B. In 1200A, both the anode and cathode are on the cryosurgical probe 1220. In 1200B, only either the anode or cathode are on the cryosurgical probe 1220. In use, cryosurgical probe 1220 may be wired as the opposite electrode.

Figure 13:
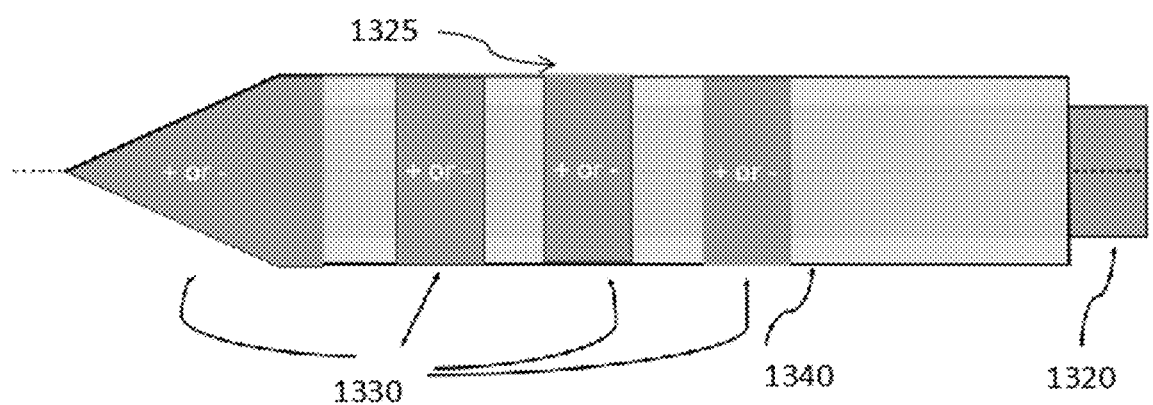
FIG. 13 is a schematic diagram of a cryosurgical instrument, according to an alternate embodiment.

FIG. 13 is a schematic drawing of another exemplary cryosurgical instrument 1325. Cryosurgical instrument 1325 includes cryosurgical probe 1320. Protective member 1340 is coupled to cryosurgical probe 1320. In the exemplary embodiment of FIG. 13, the entire cryosurgical probe 1320 is covered by protective member 1340. Cryosurgical instrument 1325 includes a plurality of electrodes 1330. Each of the electrodes 1330 can be independently wired as anodes or cathodes, as required for the delivery of the products of electrolysis.

Methods of retrofitting a cryosurgical probe are also disclosed herein. The methods may include providing a cryosurgical probe. The protective device may be used to protect an existing cryosurgical probe or replace one or more parts of an existing cryosurgical probe, such as another coating. Thus, the methods may comprise coupling the cryosurgical probe with a protective device and/or fastening the protective device to a cryosurgical probe. The methods may comprise removing one or more exterior part of a cryosurgical probe prior to coupling and/or fastening a protective device onto the cryosurgical probe.

Figure 14:
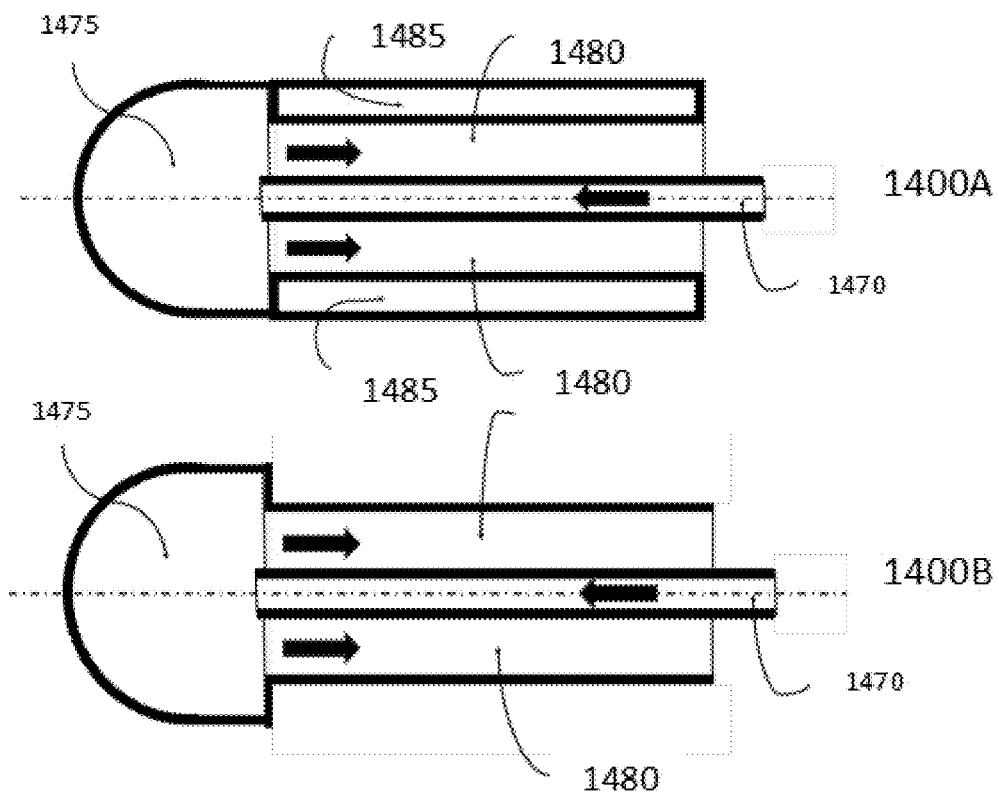
FIG. 14 is a schematic diagram of exemplary cryosurgical instruments in use, according to one embodiment.

FIG. 14 includes schematic drawings of cryosurgical instruments 1400A and 1400B in use treating tissue 10. Cryosurgical instruments 1400A and 1400B include conduit 1470 for delivery of cooling fluid (cryogen) to front chamber 1475 which contacts the target tissue for cryosurgical treatment. The walls of conduit 1470 and front chamber 1475 are designed to withstand pressure that is associated with the flow of the cooling fluid. For example, the walls of the front chamber 1475 may be formed of a material which is both thermally conductive and has the ability to withstand high pressure. Conduit 1480 is the path of the return cooling fluid from front chamber 1475. Chambers 1485 in cryosurgical probe 1400A are configured to thermally isolate the tissue from the cooling effect of the cryosurgical probe 1400A and deliver the cooling effect at a targeted location of the tissue. Chambers 1485 may be filled with air or vacuum.

Exemplary cryosurgical instruments 1400A and 1400B may be retrofit with a protective device as disclosed herein. For instance, chambers 1485 of cryosurgical instrument 1400A may be replaced with a protective device. Cryosurgical instrument 1400B may be covered or partially covered with a protective device. The resulting retrofit cryosurgical probe may be used to provide cryoelectrolytic treatment, as previously described.

Figure 15:
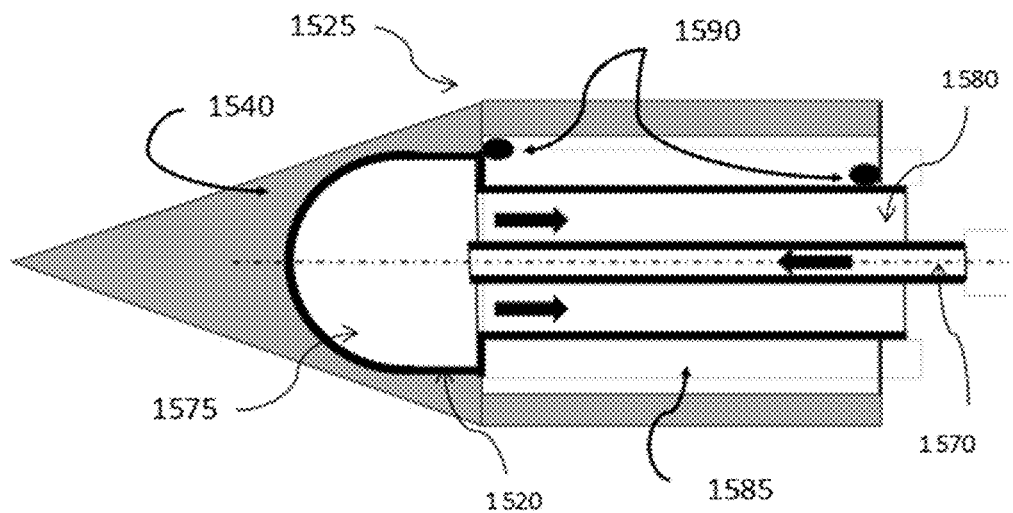
FIG. 15 is a schematic diagram of a cryosurgical instrument, according to an alternate embodiment.

FIG. 15 is a schematic drawing of another exemplary cryosurgical instrument 1525. Cryosurgical instrument 1525 includes cryosurgical probe 1520 covered by protective member 1540. Cryosurgical probe 1520 includes conduits 1570 and 1580 for the cooling fluid and front chamber 1575 for providing cryosurgical treatment upon contact with the target tissue. Chamber 1585 may thermally isolate the tissue from the effect of the cooling fluid. Chamber 1585 may be left open to air or it can be filled with an insulating material. Thermocouples 1590 may be placed in chamber 1585 at desirable locations when the chamber is left open to air. Thus, the cryosurgical probes as shown in FIG. 14 may be retrofit to include protective member 1540.

The function and advantages of these and other embodiments can be better understood from the following examples. These examples are intended to be illustrative in nature and are not considered to be limiting the scope of the invention.

EXAMPLES

Example 1: Animal Studies Showing the Effect of Electrolysis on the Materials of Cryosurgical Probes Cryosurgical probes are typically designed to withstand high pressure and to be biocompatible. Commercial cryosurgery probes were used in the experiments described below.

An R2.4 renal 2.4 mm stainless steel cryoprobe (distributed by Endocare Inc., Austin, TX USA) was tested with a single port control console device regulating flow duration and monitoring feed-back temperatures. The probe was supplied by a pressurized Argon gas container through the control console, at a constant pressure of 3000 psi. The cooling of the stainless steel cryoprobe was accomplished through a Joule-Thomson internal valve.

The cryosurgery probes also served as the electroporation/electrolysis electrodes. For electroporation, a 2510 Electroporation System power supply (distributed by Eppendorf, Hamburg, Germany) was used to generate power. For electrolysis, the metal body of the probe was connected to a DC power supply (distributed by Agilent, Santa Clara, CA USA). The experiments were performed in pigs treated in accordance with Good Laboratory Practice regulations, as set forth in 21 CFR § 58. Experiments were conducted in compliance with all ethical and legal rules imposed by national legislation and the European Union. The experiment protocol was approved by the Ethics Committee of Fundeni Clinical Institute, and by the Bucharest Sanitary-Each procedure started with anesthetization of the animal under general anesthesia per SOP #33156.

Preanesthetic medication (2.0 mL Telazol 4.0 mg/kg IM and 1.8 mL Atropine 0.02 mg/kg IM) was administered to the animals. Anesthetic induction was done by Isoflurane with oxygen at 2%/2 L/minute via mask. Possible postoperative pain was ameliorated by Buprenorphine 0.01 mg/kg IM Pre-med at recovery and Carprofen 4 mg/kg at extubation/recovery. Antibiotics administered during surgery were Cefazolin 25 mg/kg IV every 2 hours. In addition, pancuronium (0.1 mg/kg, at a dose of 1 mg/ml) was administered through an IV prior to the procedure, to reduce muscle contractions during the application of the electrical pulses. Pancuronium (0.05 mg/ml at 1 mg/ml) was administered throughout the procedure as needed.

The liver was exposed via a midline incision. Two cryosurgery probes were inserted normal to the liver outer surface, parallel to each other to a depth of 3 cm, separated by 3 cm, center to center. One of the probes served as the anode and the second as the cathode. The following protocol was applied. First, one single pulse was applied with the Eppendorf electroporation device set to 2500 V set to 1.5. The device delivered 2000 V in an exponential decay of 2.2 ms. The pulse was followed by the delivery of an electrolytic current of 70 mA for 10 minutes, which delivered a 42 Coulomb charge. The electrolytic current was followed by freezing with the cryosurgery device set at 2,800 psi Argon flow for ten minutes.

The cryosurgical probe which served as the anode failed within five minutes after the onset of freezing. Evidence of release of gas from the cryosurgical probe tip was observed. The animal studies on the combination of cryosurgery and electrolysis were stopped after equipment failure.

Thus, the combined treatments in an animal study caused failure and damage to the conventional cryosurgerical probe.

Example 2: Agar Gel Studies Showing the Effect of Electrolysis on the Materials of Cryosurgical Probes Experiments as described in Example 1 were performed in agar gels. The first electrolysis was delivered in the form of 200 mA for 10 min at 10V. Electrolysis was followed by freezing with the cryosurgery device set at 2,800 psi Argon flow for 10 min. The trocar tip of the cryoprobe that served as the anode was detached and damaged. Around the anode there was a dark rim of metal particles, which was caused by the electrolytic decomposition of the cryosurgical probe.

As in Example 1, the combined treatments in an agar gel caused failure and damage to the conventional cryosurgical probe.

Example 3: Effect of Electrolysis on the Materials of Cryosurgical Probes

Figure 16:
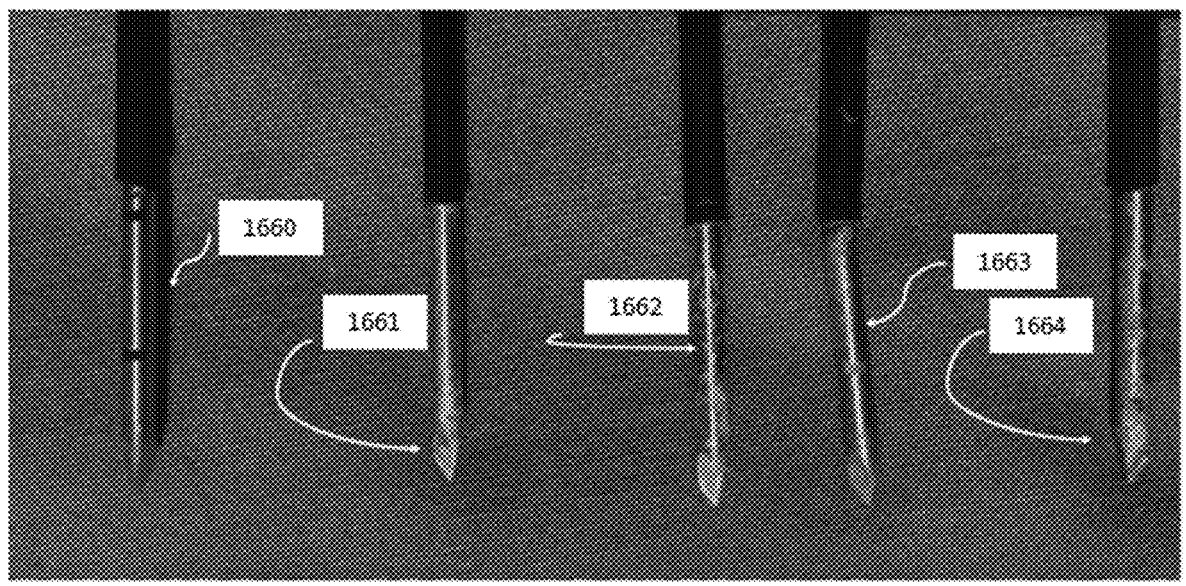
FIG. 16 is a photograph of exemplary cryosurgical instruments after use, according to one embodiment.

Experiments as described in Examples 1 and 2 were performed on various cryosurgical probes. Photographs of the damaged probes (anode and cathode) are shown in FIG. 16. Briefly, freezing was delivered first. After 10 minutes of freezing, the cooling was ceased and an electrolytic current of 100 mA at 40 V was delivered for 10 minutes. As seen in the photographs of FIG. 16, cryosurgery probes 1661, 1662, 1663, and 1664 are damaged. These cryosurgery probes served as the anode. Cryosurgery probe 1660, which served as the cathode, appears to have suffered from less damage.

Example 4: Effect of Electrolysis on Aluminum Coated Cryosurgical Probes

It is believed that an effective placement of the electrodes in cryoelectrolysis is correlated with the placement of the cryosurgery probe. The location may be selected to provide a superposition of the region affected by electrolysis on the region affected by freezing. Since conventional cryosurgery probes are made of electrically conductive materials, they may be used as the electrode. However, the findings in Examples 1-3 show that electrolysis can damage the material of the cryosurgery probe, and patient safety requires a different technology for enabling the combination electrolysis generating electrical currents in cryoelectrolysis, cryoelectroporation, and cryoelectrolytic-electroporation and freezing.

Figure 17:
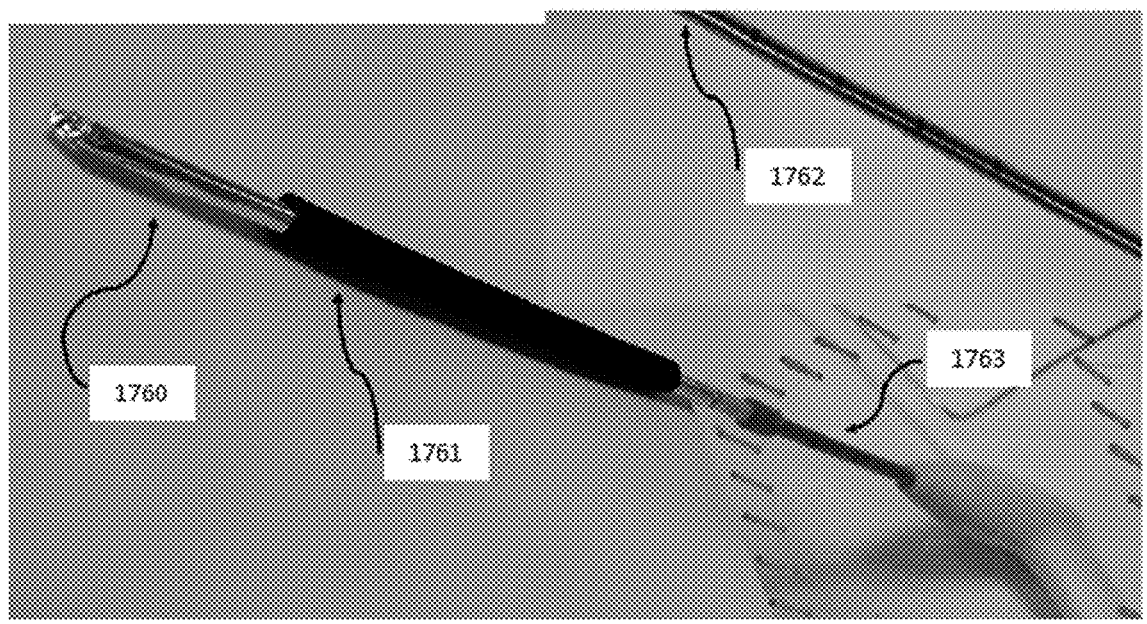
FIG. 17 is a photograph of exemplary cryosurgical instruments after use, according to one embodiment.

One embodiment of a safe cryoelectric probe is shown in FIG. 17. FIG. 17 shows the components and the assembly of a cryoelectric device 1763, according to an embodiment described herein. The device shown in FIG. 17 may be assembled on a conventional cryosurgery probe, for example, an R2.4 cryosurgery probe as described above. A higher magnification detail of the shaft and tip of the probe is shown in 1762. The cryoprobe base was insulated using a shrinking tube 1761 having an inner diameter of 2.5 m and a tube wall thickness 0.2 mm. A strip of 4 cm×3 cm of an aluminum sheet 1760 having a thickness of 0.5 mm was tightly wrapped around the cryosurgical probe. The active part of the cryosurgical probe, which was covered by the aluminum sheet, was 3 cm from the probe tip. The distal end was tapered around the tip to simulate a conical tip, similar to that of the cryosurgical probe. The design was similar to the embodiment described in FIG. 2.

Aluminum was selected as a material with good thermal and electrical conductivity. Therefore, the aluminum did not interfere with heat transfer from the cryosurgery probe. When the power supply was connected to the metal shaft of the cryosurgical probe, the electrical charge became distributed on the outer surface of the aluminum sheet, which served as the electrode and protected the cryosurgical electrode.

Figure 18:
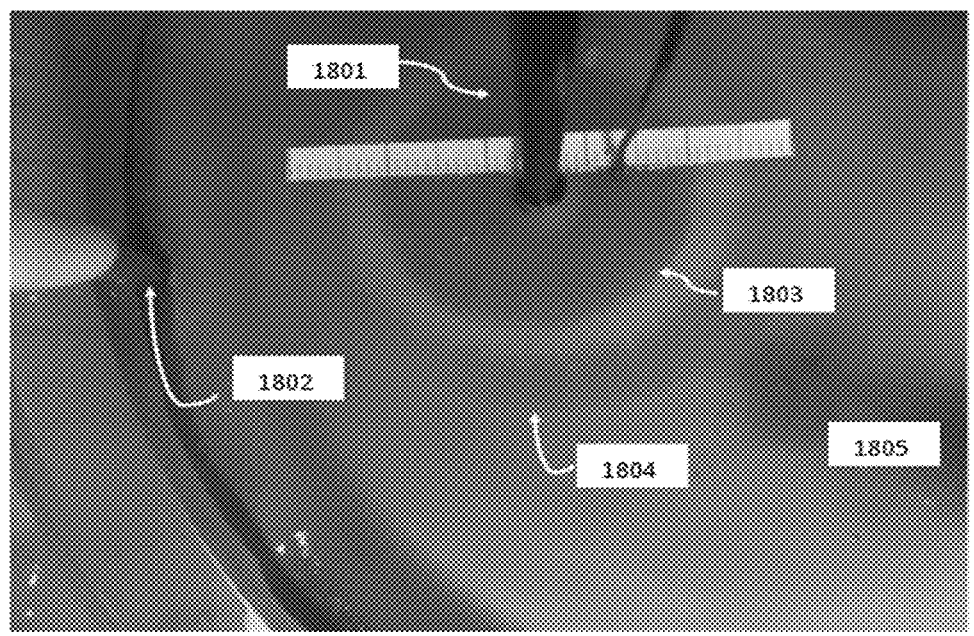
FIG. 18 is a photograph of exemplary cryosurgical instruments after use, according to one embodiment.

An experiment was performed in which the cryosurgical probe shaft was connected to the power supply as the anode. The results are shown in FIG. 18. The cryosurgical probe/anode 1801 was inserted in an agar gel made of a physiological saline composition-filled basin 1805. The gel was stained with a pH sensitive dye. The cryosurgical probe was inserted to a depth of 3 cm, such that the entire aluminum cover part was inside the gel and only the insulated part protruded from the gel. A copper electrode was inserted circumferentially around the gel 1802 to serve as the cathode. The cryosurgical probe was operated to freeze the gel until a 5 cm diameter ice ball 1804 was observed. At the end of freezing a current of 200 mA at 50 V was applied for 10 mins. A variation in color 1803 was observed. The variation is a result of the pH dye and demonstrates substantial generation of electrolytic products.

Figure 19:
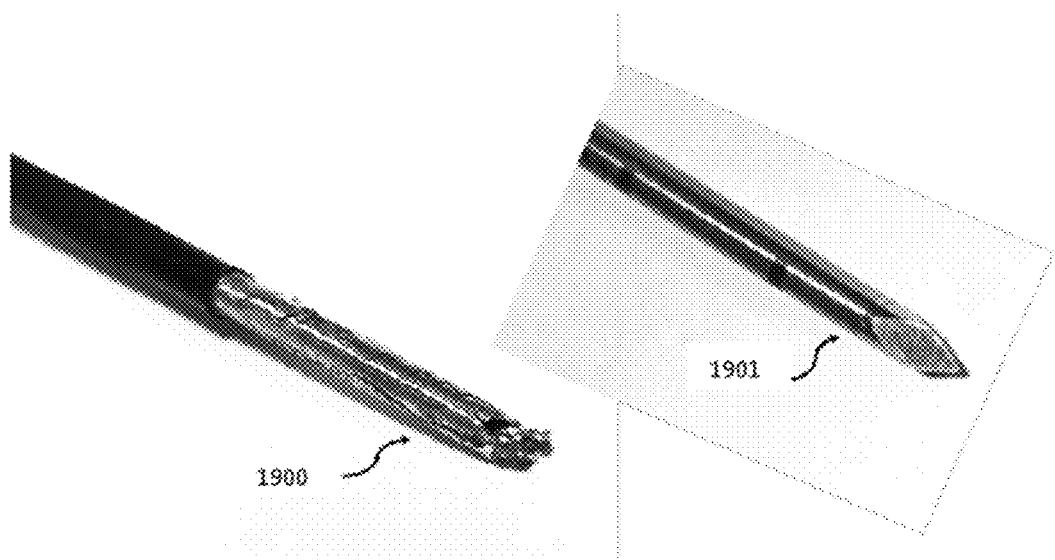
FIG. 19 is a photograph of exemplary cryosurgical instruments after use, according to one embodiment.

An experiment was performed in which a coating as described herein was used to protect the cryosurgical probe, which also served as the anode. The results are shown in FIG. 19. As seen in FIG. 19, partial damage to the aluminum coating on the cryosurgical probe was observed and the tip 1900 was totally destroyed. However, the cryosurgical probe 1901 was intact. The outcome of using a coating can be appreciated when comparing the coated cryosurgical probe shown in FIG. 19 with the un-coated cryosurgical probes that served as anodes as shown in FIG. 16.

Thus, the coated cryosurgical probes can withstand electrolysis more effectively than un-coated cryosurgical probes.

Figure 20:
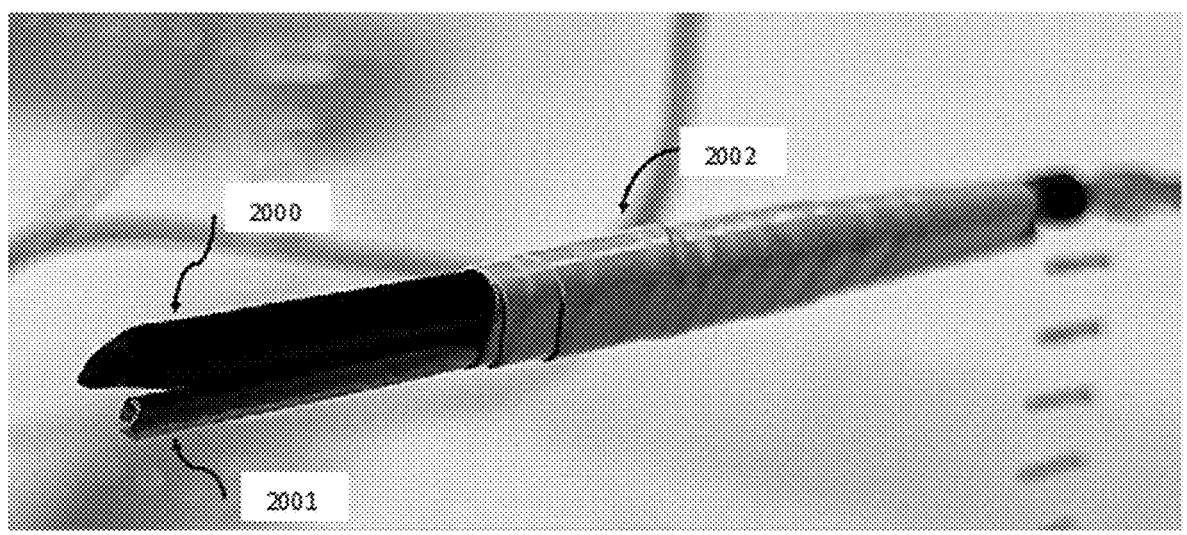
FIG. 20 is a photograph of exemplary cryosurgical instruments after use, according to one embodiment.

Example 5: Effect of Electrolysis on Heat Shrinking Wrap Coated Cryosurgical Probes A conventional cryosurgical probe was completely wrapped with a thin heat shrinking tube 2000 having an inner diameter of 2.5 mm and a tube wall thickness of 0.2 mm, as shown in FIG. 20. Heat shrinking wrap is ordinarily made of nylon or polyolefin, which shrinks radially (but not longitudinally) when heated, to between one-half and one-sixth of its diameter. The heat shrinking wrap served to electrically isolate the cryosurgical probe from the process of electrolysis. A stainless steel electrode 2001 having a 2 mm diameter was attached to the cryosurgical probe with an electrically insulating tape 2002, leaving 3.5 cm of the distal end of the electrode uncovered. The cryosurgical probe was tested as described in Example 4.

As shown in FIG. 20, the steel anode 2001 was partially damaged but the cryosurgical probe was intact. The coated cryosurgical probes can withstand electrolysis.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

What is claimed is:

1. A cryosurgical instrument comprising:
  a cryosurgical probe configured to deliver a cryosurgical treatment to a target tissue;
  at least one electrode configured to generate products of electrolysis at the target tissue; and
  a protective member coupled to at least a portion of an exterior surface of the cryosurgical probe, effective to substantially isolate the cryosurgical probe from the products of electrolysis,
  wherein the protective member is formed of a material effective to substantially isolate the cryosurgical probe from products of electrolysis and being dimensioned to conform to the at least the portion of the exterior surface of the cryosurgical probe,
  wherein the material of the protective member is more anodic than a material of the cryosurgical probe.

2. The cryosurgical instrument of claim 1, wherein the protective member is thermally conductive.

3. The cryosurgical instrument of claim 1, wherein the at least one electrode is fastened to the cryosurgical probe.

4. The cryosurgical instrument of claim 3, wherein the at least one electrode is fastened to a portion of the exterior surface of the cryosurgical probe adjacent to the protective member.

5. The cryosurgical instrument of claim 4, wherein the at least one electrode is thermally conductive.

6. The cryosurgical instrument of claim 4, wherein at least one electrode and the protective member is movable along the exterior surface of the cryosurgical probe.

7. The cryosurgical instrument of claim 1, wherein the at least one electrode is electrically wired as an anode and the cryosurgical probe is electrically wired as a cathode.

8. The cryosurgical instrument of claim 1, further comprising a vacuum layer between the exterior surface of the cryosurgical probe and the protective member.

9. The cryosurgical instrument of claim 8, wherein the vacuum layer is movable along the exterior surface of the cryosurgical probe.

10. The cryosurgical instrument of claim 1, wherein the protective member is removable from the cryosurgical instrument.

11. The cryosurgical instrument of claim 1, wherein the protective member is configured to have a thickness effective to substantially isolate the cryosurgical probe from products of electrolysis when conformed to the at least the portion of the exterior surface of the cryosurgical probe.

12. A method of providing combined cryosurgical treatment and electrolysis, comprising bringing the cryosurgical instrument of claim 1 into contact with the target tissue, delivering a cryosurgical treatment to the target tissue and generating products of electrolysis at the target tissue.

13. The method of claim 12, wherein the cryosurgical treatment comprises cooling to a temperature of between about 0° C. and about −40° C. and the products of electrolysis are generated by an electrical current of between about 10 mA/cm$^2$ electrode surface to 200 mA/cm$^2$ electrode surface at a voltage of between about 5 V to 50 V.

14. The method of claim 12, comprising independently controlling dosage, timing, and magnitude of the cryosurgical treatment and the electrolysis.

15. A cryosurgical system comprising:
  a cryosurgical instrument comprising a cryosurgical probe configured to deliver a cryosurgical treatment to a target tissue, at least one electrode configured to generate products of electrolysis at the target tissue, and a protective member coupled to at least a portion of an exterior surface of the cryosurgical probe, effective to substantially isolate the cryosurgical probe from the products of electrolysis, wherein the protective member is formed of a material effective to substantially isolate the cryosurgical probe from products of electrolysis and being dimensioned to conform to the at least the portion of the exterior surface of the cryosurgical probe, wherein the material of the protective member is more anodic than a material of the cryosurgical probe;
  a cryogenic power supply electrically connected to the cryosurgical probe;
  an electrolysis power supply electrically connected to the at least one electrode; and
  a controller operatively connected to the cryogenic power supply and the electrolysis power supply, the controller configured to generate a cryogenic signal and an electric signal.

16. The system of claim 15, wherein the controller is configured to control at least one parameter selected from dosage, timing, and magnitude of the cryosurgical treatment and the electrolysis.

17. The system of claim 15, further comprising a pH sensor positioned to measure pH at the target tissue.

18. The system of claim 17, wherein the pH sensor is operatively connected to the controller and the controller is configured to generate the electric signal responsive to the pH measurement.

19. The system of claim 15, further comprising an electric meter positioned to measure electric field strength at the target tissue.

20. The system of claim 19, wherein the electric meter is operatively connected to the controller and the controller is configured to generate the electric signal responsive to the electric field strength.

21. A method of producing a cryosurgical instrument, comprising:
  selecting a cryosurgical probe configured to deliver a cryosurgical treatment to a target tissue;

coupling at least one electrode configured to generate products of electrolysis to the cryosurgical probe; and fastening a protective member to at least a portion of an exterior surface of the cryosurgical probe, effective to substantially isolate the cryosurgical probe from the products of electrolysis, wherein the protective member is formed of a material effective to substantially isolate the cryosurgical probe from products of electrolysis and being dimensioned to conform to the at least the portion of the exterior surface of the cryosurgical probe, wherein the material of the protective member is more anodic than a material of the cryosurgical probe.

22. The method of claim 21, comprising selecting a material for the protective member to be thermally conductive and more anodic than a material of the cryosurgical probe.

23. The method of claim 21, further comprising positioning a vacuum layer between the external surface of the cryosurgical probe and the protective member.

\* \* \* \* \*